US009764009B2

(12) United States Patent
Abel et al.

(10) Patent No.: US 9,764,009 B2
(45) Date of Patent: Sep. 19, 2017

(54) TREATMENT OF PSYCHOLOGICAL TRAUMA

(75) Inventors: Kenton B. Abel, Hacienda Heights, CA (US); Andrew M. Blumenfeld, Del Mar, CA (US)

(73) Assignee: Allergan, Inc., Irvine, CA (US)

( * ) Notice: Subject to any disclaimer, the term of this patent is extended or adjusted under 35 U.S.C. 154(b) by 438 days.

(21) Appl. No.: 13/495,605

(22) Filed: Jun. 13, 2012

(65) Prior Publication Data

US 2012/0315297 A1 Dec. 13, 2012

Related U.S. Application Data

(60) Provisional application No. 61/496,192, filed on Jun. 13, 2011.

(51) Int. Cl.
*A61K 38/48* (2006.01)

(52) U.S. Cl.
CPC ................................ *A61K 38/4893* (2013.01)

(58) Field of Classification Search
None
See application file for complete search history.

(56) References Cited

U.S. PATENT DOCUMENTS 5,714,468 A 2/1998 Binder
6,500,436 B2 12/2002 Donovan
6,641,820 B1 11/2003 Donovan
7,056,729 B2 6/2006 Donovan
7,132,259 B1 11/2006 Dolly
7,138,127 B1 11/2006 Donovan
7,244,436 B2 7/2007 Donovan
7,244,437 B2 7/2007 Donovan
7,262,291 B2 8/2007 Donovan
7,354,740 B2 4/2008 Xiang
7,413,742 B2 8/2008 Donovan
7,419,676 B2 9/2008 Dolly
7,422,877 B2 9/2008 Dolly
7,425,338 B2 9/2008 Donovan
7,449,515 B2 * 11/2008 Belelie et al. ................ 524/589
7,514,088 B2 4/2009 Steward
7,622,127 B2 11/2009 Donovan
7,655,244 B2 * 2/2010 Blumenfeld ............... 424/239.1
7,658,933 B2 2/2010 Foster
7,659,092 B2 2/2010 Foster
7,704,512 B2 4/2010 Donovan
7,709,228 B2 5/2010 Dolly
7,736,659 B2 6/2010 Donovan
7,740,868 B2 6/2010 Steward
7,749,514 B2 7/2010 Steward
7,780,968 B2 8/2010 Donovan
7,811,584 B2 10/2010 Steward
7,811,587 B2 10/2010 Donovan
7,833,535 B2 11/2010 Donovan
7,897,157 B2 3/2011 Steward
7,959,933 B2 6/2011 Dolly
7,981,433 B2 * 7/2011 Blumenfeld ............... 424/239.1
8,241,641 B2 * 8/2012 Blumenfeld ............... 424/239.1
8,383,103 B2 * 2/2013 Gaylis et al. .............. 424/94.62
8,388,952 B2 * 3/2013 Gaylis et al. .............. 424/94.62
8,420,106 B1 * 4/2013 Binder ....................... 424/239.1
8,491,917 B1 * 7/2013 Bender ...................... 424/239.1
8,609,112 B2 * 12/2013 Blumenfeld et al. ...... 424/247.1
8,609,113 B2 * 12/2013 Blumenfeld et al. ...... 424/247.1
8,617,569 B2 * 12/2013 Binder ....................... 424/239.1
8,697,066 B2 * 4/2014 Gaylis et al. .............. 424/94.62
8,722,606 B2 * 5/2014 Creamer et al. .............. 510/230
8,734,810 B2 * 5/2014 Blumenfeld ............... 424/239.1
8,846,622 B2 * 9/2014 Blumenfeld ......... A61K 9/0014 424/239.1
8,992,941 B2 * 3/2015 Blumenfeld ....... A61K 38/4893 424/239.1
9,238,061 B2 * 1/2016 Blumenfeld ....... A61K 38/4893
9,248,168 B2 * 2/2016 Blumenfeld ....... A61K 38/4893
2005/0191320 A1 9/2005 Turkel
2008/0057575 A1 3/2008 Fernandez-Salas
2008/0138893 A1 6/2008 Steward
2008/0241881 A1 10/2008 Steward
2008/0317783 A1 12/2008 Donovan
2009/0004224 A1 1/2009 Steward
2009/0005313 A1 1/2009 Steward
2009/0018081 A1 1/2009 Steward
2009/0030182 A1 1/2009 Dolly
2009/0042270 A1 2/2009 Dolly
2009/0069238 A1 3/2009 Steward
2009/0081730 A1 3/2009 Dolly
2009/0087458 A1 4/2009 Dolly
2009/0162341 A1 6/2009 Foster (Continued)

FOREIGN PATENT DOCUMENTS

WO 2006-099590 9/2006
WO 2006-101809 9/2006

(Continued)

OTHER PUBLICATIONS

Gaffney, "Established and Emerging PTSD Treatments"; Mental Health Clinician, 2013, 2/7:35; available at: http://cpnp.org/resource/mhc/2013/01/establised-and-emerging-ptsd-treatments.*
Rosenthal et al, Headache, 2013, 53:1564-1572.*
Blumenfeld et al, Headache, 2010, 50:1406-1418.*
Ansel, Howard, Pharmaceutical Dosage Forms and Drug Delivery Systems, 1999, 2 Pages, 7th edition, Lippincott Williams & Wilkins.
Gennaro, Alfonso, Remington: The Science and Practice, 2000, 2 Pages, 20th edition, Lippincott Williams & Wilkins.
Goodman & Gilman's The Pharmacological Basis of Therapeutics, 10th Edition, McGraw-Hill, 2001, 2 pages.
Lipham, William, Cosmetic and Clinical Applications of Botulinum Toxin, 2004, 2 Pages, Slack Inc.
Rowe, Raymond, Handbook of Pharmaceutical Excipients, 2003, 2 Pages, 4th edition, Pharmceutical Press.
Schantz, Edward J. et al, Properties and Use of Botulinum Toxin and Other Microbial Nerotoxins in Medicine, Microbiological Reviews, Mar. 1992, 80-99, 56 (1), US.

*Primary Examiner* — Nita M Minnifield
(74) *Attorney, Agent, or Firm* — Brigitte C. Phan; Ted A. Chan

(57) ABSTRACT

The present specification discloses methods of treating a psychological trauma in an individual using botulinum toxins and/or a Targeted Exocytosis Modulator, and compositions thereof.

2 Claims, 7 Drawing Sheets

(56) References Cited

U.S. PATENT DOCUMENTS

| | | | | |
|---|---|---|---|---|
| 2010/0034802 | A1 | 2/2010 | Foster | |
| 2010/0041098 | A1 | 2/2010 | Steward | |
| 2010/0247509 | A1 | 9/2010 | Foster | |
| 2011/0027256 | A1 | 2/2011 | Foster | |
| 2011/0070621 | A1 | 3/2011 | Steward | |
| 2011/0091437 | A1 | 4/2011 | Foster | |
| 2011/0189162 | A1 | 8/2011 | Ghanshani | |
| 2012/0264703 | A1* | 10/2012 | Khan et al. | 514/25 |
| 2012/0315297 | A1* | 12/2012 | Abel et al. | 424/239.1 |
| 2014/0079687 | A1* | 3/2014 | Blumenfeld | 424/94.67 |
| 2014/0099298 | A1* | 4/2014 | Blumenfeld | 424/94.67 |
| 2014/0205590 | A1* | 7/2014 | Blumenfeld | 424/94.67 |
| 2016/0151468 | A1* | 6/2016 | Blumenfeld | A61K 38/4893 424/94.67 |
| 2016/0263202 | A1* | 9/2016 | Blumenfeld | A61K 38/4893 |

FOREIGN PATENT DOCUMENTS

| | | |
|---|---|---|
| WO | 2007-106115 | 9/2007 |
| WO | 2008-008803 | 1/2008 |
| WO | 2008-008805 | 1/2008 |
| WO | 2008-105901 | 9/2008 |
| WO | 2010-090677 | 8/2010 |
| WO | 2011-020052 | 2/2011 |
| WO | 2011-020056 | 2/2011 |
| WO | 2011-020114 | 2/2011 |
| WO | 2011-020115 | 2/2011 |
| WO | 2011-020117 | 2/2011 |
| WO | 2011-020119 | 2/2011 |
| WO | 2011-091370 | 7/2011 |
| WO | WO 2012/174123 A1 * | 12/2012 |
| WO | WO 2013/137969 A1 * | 9/2013 |
| WO | WO 2014/078724 A1 * | 5/2014 |

* cited by examiner

TREATMENT OF PSYCHOLOGICAL TRAUMA

This application claims the benefit of priority pursuant to 35 U.S.C. §119(e) to U.S. provisional patent application Ser. No. 61/496,192, filed Jun. 13, 2011 and incorporated entirely by reference.

Psychological trauma is a type of damage to the psyche that occurs as a result of a traumatic event. A traumatic event involves a single experience, or an enduring or repeating event or events, that completely overwhelm the individual's ability to cope or integrate the ideas and emotions involved with that experience. The sense of being overwhelmed can be delayed by weeks, years or even decades, as the person struggles to cope with the immediate circumstances. intense feelings of anger may surface frequently, sometimes in very inappropriate or unexpected situations, as danger may always seem to be present. Upsetting memories such as images, thoughts, or flashbacks may haunt the person, and nightmares may be frequent. Insomnia may occur as lurking fears and insecurity keep the person vigilant and on the lookout for danger, both day and night.

Post-traumatic stress disorder (PTSD) is a severe anxiety disorder that can develop after exposure to any event that results in psychological trauma. A common example of an event triggering PTSD is the repeated threat of death to oneself or a companion, such as during combat operations. Many soldiers experience PTSD after returning from a war. Other examples of events leading to PTSD include threats or assaults on the physical, sexual, or psychological integrity to oneself or a companion. The psychological trauma overwhelms the individual's ability to cope. PTSD may be more likely to be caused by physical or psychological trauma caused by humans such as rape, war, or terrorist attack than trauma caused by natural disasters. Symptoms for PTSD include re-experiencing the original trauma(s) through flashbacks or nightmares, avoidance of stimuli associated with the trauma, and increased arousal—such as difficulty falling or staying asleep, anger, and hyper-vigilance. Findings indicate that a failure to provide adequate treatment to children after they suffer a traumatic experience, depending on their vulnerability and the severity of the trauma, will ultimately lead to PTSD symptoms in adulthood. PTSD symptoms may result when a traumatic event causes an overactive adrenaline response, which creates deep neurological patterns in the brain. These patterns can persist long after the event that triggered the fear, making an individual hyper-responsive to future fearful situations.

One of the first descriptions of PTSD was made by the Greek historian Herodotus in 490 BCE. He described, during the Battle of Marathon, an Athenian soldier who suffered no injury from war but became permanently blind after witnessing the death of a fellow soldier. Previous diagnoses now considered historical equivalents of PTSD include railway spine, stress syndrome, shell shock, battle fatigue, or traumatic war neurosis. Even after 2,500 years, while a variety of medications have shown adjunctive benefit in reducing PTSD symptoms, there is no clear drug treatment for PTSD.

Complex post-traumatic stress disorder (C-PTSD) is a psychological injury that results from protracted exposure to prolonged social and/or interpersonal trauma with lack or loss of control, disempowerment, and in the context of either captivity or entrapment. C-PTSD is distinct from, but similar to, PTSD. The present invention includes the treatment of C-PTSD.

BRIEF DESCRIPTION OF THE DRAWINGS

FIG. 1 shows a schematic of the current paradigm of neurotransmitter release and Clostridial toxin intoxication in a central and peripheral neuron.

FIG. 3 shows Targeted Exocytosis Modulator (TEM) domain organization with a targeting domain located at the amino terminus of a TEM.

FIG. 4 shows a TEM domain organization with a targeting domain located between the other two domains.

FIG. 5 shows a TEM domain organization with a targeting domain located at the carboxyl terminus of the TEM.

DESCRIPTION

Figure 1A:
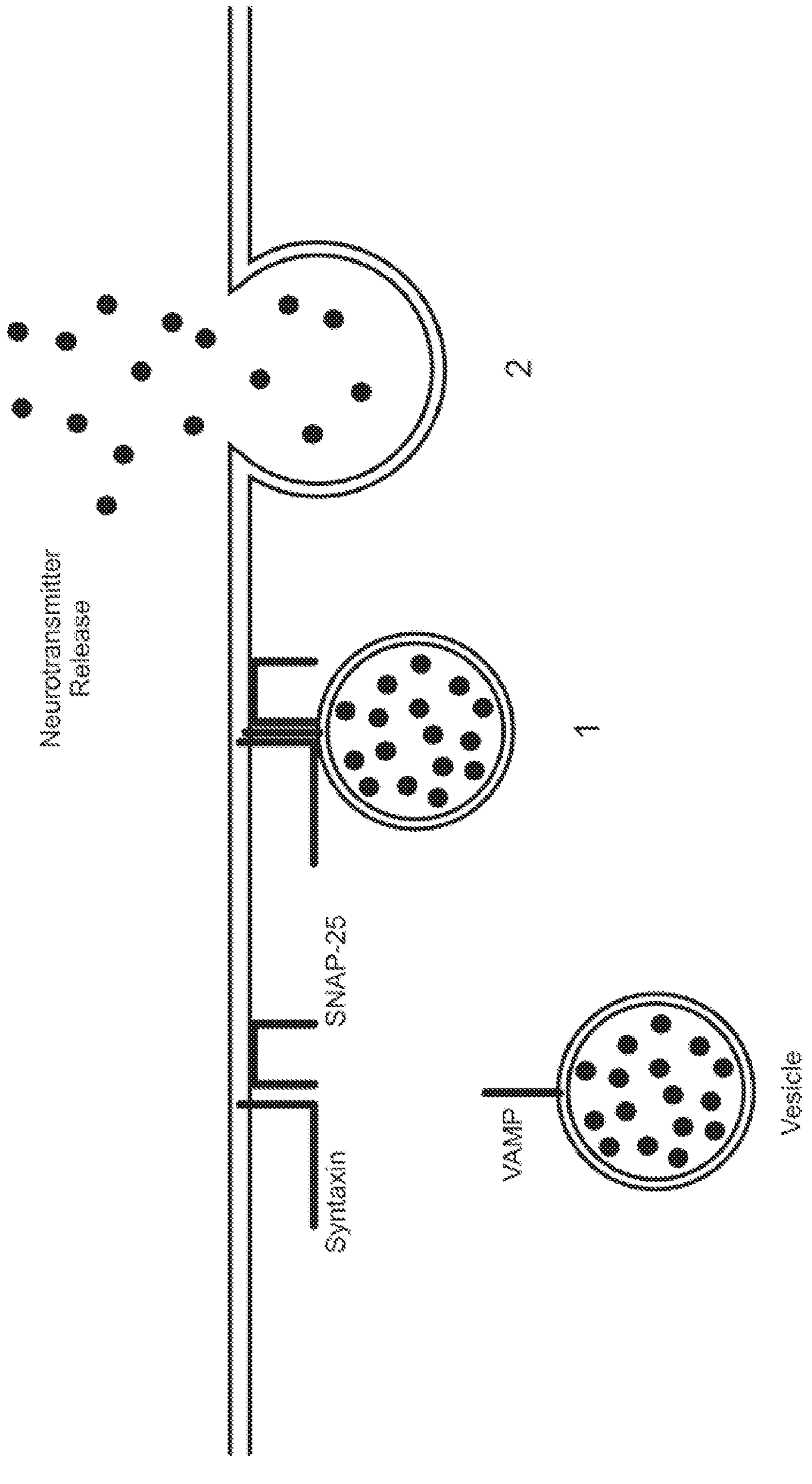
FIG. 1A shows a schematic for the neurotransmitter release mechanism of a central and peripheral neuron. The release process can be described as comprising two steps: 1) vesicle docking, where the vesicle-bound SNARE protein of a vesicle containing neurotransmitter molecules associates with the membrane-bound SNARE proteins located at the plasma membrane; and 2) neurotransmitter release, where the vesicle fuses with the plasma membrane and the neurotransmitter molecules are exocytosed.

For purposes of this application, any BoNT units are given in terms of Botox® units. Therapeutically effective units of other BoNT products, such as Xeomin® and Dysport®, may be titrated by one of ordinary skill in the art.

The ability of Clostridial toxins, such as, e.g., Botulinum neurotoxins (BoNTs), BoNT/A, BoNT/B, BoNT/C1, BoNT/D, BoNT/E, BoNT/F and BoNT/G, and Tetanus neurotoxin (TeNT), to inhibit neuronal transmission are being exploited in a wide variety of therapeutic and cosmetic applications, see e.g., William J. Lipham, Cosmetic and Clinical Applications of Botulinum Toxin (Slack, ed., 2004). Clostridial toxins commercially available as pharmaceutical compositions include, BoNT/A preparations, such as, e.g., BOTOX® (Allergan, Inc., Irvine, Calif.), DYSPORT®/RELOXIN®, (Beaufour Ipsen, Porton Down, England), NEURONOX® (Medy-Tox, Inc., Ochang-myeon, South Korea), BTX-A (Lanzhou Institute Biological Products, China) and XEOMIN® (Merz Pharmaceuticals, GmbH., Frankfurt, Germany); and BoNT/B preparations, such as, e.g., MYOBLOC™/NEUROBLOC™ (Solstice Neurosciences, Inc., South San Francisco, Calif.). As an example, BOTOX® is currently approved in one or more countries for the following indications: achalasia, adult spasticity, anal fissure, back pain, blepharospasm, bruxism, cervical dystonia, essential tremor, glabellar lines or hyperkinetic facial lines, headache, hemifacial spasm, hyperactivity of bladder, hyperhidrosis, juvenile cerebral palsy, multiple sclerosis, myoclonic disorders, nasal labial lines, spasmodic dysphonia, strabismus and VII nerve disorder. See also, U.S. Pat. No. 5,714,468 (migraine) issued Feb. 3, 1998; Published U.S. Patent Application No. 2005019132 (headache), Ser. No. 11/039,506, filed Jan. 18, 2005; Published U.S. Patent Application No. 20050191320 (medication overuse headache), Ser. No. 10/789,180, filed Feb. 26, 2004; and U.S. Pat. No. 7,811,587 (neuropsychiatric disorders), issued Oct. 12, 2010; U.S. application Ser. No. 13/053,583, filed Mar. 22, 2011 (depression); and, U.S. application Ser. No. 13/075,485, filed Mar. 30, 2011 (migraine treatment), all incorporated entirely by reference.

Clostridial toxin therapies have been successfully used for many indications. However, toxin administration in some applications can be challenging because of the larger doses required to achieve a beneficial effect. Larger doses can increase the likelihood that the toxin may move through the interstitial fluids and the circulatory systems, such as, e.g., the cardiovascular system and the lymphatic system, of the body, resulting in the undesirable dispersal of the toxin to areas not targeted for toxin treatment. Such dispersal can lead to undesirable side effects, such as, e.g., inhibition of neurotransmitter release in neurons not targeted for treatment or paralysis of a muscle not targeted for treatment. For example, a individual administered a therapeutically effective amount of a BoNT/A treatment into the neck muscles for cervical dystonia may develop dysphagia because of dispersal of the toxin into the oropharynx. As another example, a individual administered a therapeutically effective amount of a BoNT/A treatment into the bladder for overactive bladder may develop dry mouth and/or dry eyes. Thus, there still remains a need for treatments having the therapeutic effects that only larger doses of a Clostridial toxin can currently provide, but reduce or prevent the undesirable side-effects associated with larger doses of a Clostridial toxin administration.

*Clostridia* toxins produced by *Clostridium botulinum, Clostridium tetani, Clostridium baratii* and *Clostridium butyricum* are the most widely used in therapeutic and cosmetic treatments of humans and other mammals. Strains of *C. botulinum* produce seven antigenically-distinct types of Botulinum toxins (BoNTs), which have been identified by investigating botulism outbreaks in man (BoNT/A, BoNT/B, BoNT/E and BoNT/F), animals (BoNT/C1 and BoNT/D), or isolated from soil (BoNT/G). BoNTs possess approximately 35% amino acid identity with each other and share the same functional domain organization and overall structural architecture. It is recognized by those of skill in the art that within each type of Clostridial toxin there can be subtypes that differ somewhat in their amino acid sequence, and also in the nucleic acids encoding these proteins. For example, there are presently five BoNT/A subtypes, BoNT/A1, BoNT/A2, BoNT/A3 BoNT/A4 and BoNT/A5, with specific subtypes showing approximately 89% amino acid identity when compared to another BoNT/A subtype. While all seven BoNT serotypes have similar structure and pharmacological properties, each also displays heterogeneous bacteriological characteristics. In contrast, tetanus toxin (TeNT) is produced by a uniform group of *C. tetani*. Two other *Clostridia* species, *C. baratii* and *C. butyricum*, produce toxins, BaNT and BuNT, which are functionally similar to BoNT/F and BoNT/E, respectively.

A Clostridial toxin treatment inhibits neurotransmitter release by disrupting the exocytotic process used to secret the neurotransmitter into the synaptic cleft. There is a great desire by the pharmaceutical industry to expand the use of Clostridial toxin therapies beyond its current myorelaxant applications to treat sensory, sympathetic, and/or parasympathetic nerve-based ailments, such as, e.g., various kinds of smooth muscle-based disorders. One approach that is currently being exploited involves modifying a Clostridial toxin such that the modified toxin has an altered cell targeting capability for a neuronal or non-neuronal cell of interest. Called re-targeted endopeptidases or Targeted Vesicular Exocytosis Modulator Proteins (TVEMPs) or Targeted Exocytosis Modulators (TEMs), these molecules achieve their exocytosis inhibitory effects by targeting a receptor present on the neuronal or non-neuronal target cell of interest. This re-targeted capability is achieved by replacing the naturally-occurring binding domain of a Clostridial toxin with a targeting domain showing a selective binding activity for a non-Clostridial toxin receptor present in a cell of interest. Such modifications to the binding domain result in a molecule that is able to selectively bind to a non-Clostridial toxin receptor present on the target cell. A re-targeted endopeptidase can bind to a target receptor, translocate into the cytoplasm, and exert its proteolytic effect on the SNARE complex of the neuronal or non-neuronal target cell of interest.

The present specification discloses methods for treating an individual suffering from physiological trauma disorders. This is accomplished by administering a therapeutically effective amount of a composition comprising a Botulinum toxin (BoNT) and/or a TEM to an individual in need thereof. The disclosed methods provide a safe outpatient-based treatment.

With reference to psychological trauma disorders as disclosed herein, and without wishing to be limited by any particular theory, it is believed that sympathetic, parasympathetic, and/or sensory neurons have important functions in aspects of psychological trauma regulation and that improper innervations from these types of neurons can contribute to one or more different types of psychological trauma disorders. As such, TEMs comprising a targeting domain for a receptor present on sympathetic, parasympathetic, and/or sensory neurons can reduce or prevent these improper innervations, thereby reducing or preventing one or more symptoms associate with a psychological trauma disorder. It is further theorized that such a TEM in combination with a Clostridial toxin can provide enhanced, if not synergistic, therapeutic benefit because such a combination also inhibit motor neurons. However, using a combination therapy of such a TEM with a Clostridial toxin, also allows a lower dose of a Clostridial toxin to be administered to treat a psychological trauma disorder. This will result in a decrease in muscle weakness generated in the compensatory muscles relative to the current treatment paradigm. As such, a combined therapy using a Clostridial toxin and a TEM comprising a targeting domain for a receptor present on sympathetic, parasympathetic, and/or sensory neurons can reduce or prevent these improper innervations, and in combination can reduce or prevent one or more symptoms associate with a psychological trauma disorder.

Thus, aspects of the present specification disclose methods of treating a psychological trauma disorder in an individual, the methods comprising the step of administering to the individual in need thereof a therapeutically effective amount of a composition including a TEM, wherein administration of the composition reduces a symptom of the psychological trauma disorder, thereby treating the individual. In some aspects, a TEM may comprise a targeting domain, a Clostridial toxin translocation domain and a Clostridial toxin enzymatic domain. In some aspects, a TEM may comprise a targeting domain, a Clostridial toxin translocation domain, a Clostridial toxin enzymatic domain, and an exogenous protease cleavage site. A targeting domain includes, without limitation, a sensory neuron targeting domain, a sympathetic neuron targeting domain, or a parasympathetic neuron targeting domain.

Other aspects of the present specification disclose uses of a TEM disclosed herein in the manufacturing a medicament for treating a psychological trauma disorder disclosed herein in an individual in need thereof.

Yet other aspects of the present specification uses of a TEM disclosed herein in the treatment of a psychological trauma disorder disclosed herein in an individual in need thereof.

Other aspects of the present specification disclose methods of treating a psychological trauma disorder in an individual, the methods comprising the step of administering to the individual in need thereof a therapeutically effective amount of a composition including a Clostridial neurotoxin and a TEM, wherein administration of the composition reduces a symptom of the psychological trauma, thereby treating the individual. A Clostridial neurotoxin includes, without limitation, a Botulinum toxin (BoNT), a Tetanus toxin (TeNT), a *Baratii* toxin (BaNT), and a *Butyricum* toxin (BuNT). In some aspects, a TEM may comprise a targeting domain, a Clostridial toxin translocation domain and a Clostridial toxin enzymatic domain. In some aspects, a TEM may comprise a targeting domain, a Clostridial toxin translocation domain, a Clostridial toxin enzymatic domain, and an exogenous protease cleavage site. A targeting domain includes, without limitation, a sensory neuron targeting domain, a sympathetic neuron targeting domain, or a parasympathetic neuron targeting domain.

Other aspects of the present specification disclose uses of a Clostridial neurotoxin and a TEM disclosed herein in the manufacturing a medicament for treating a psychological trauma disorder disclosed herein in an individual in need thereof.

Yet other aspects of the present specification uses of a Clostridial neurotoxin and a TEM disclosed herein in the treatment of a psychological trauma disorder disclosed herein in an individual in need thereof.

As used herein, "about" means approximately or nearly and in the context of a numerical value or range set forth means±15% of the numerical value range recited.

As used herein, "neurotoxin" means a biologically active molecule with a specific affinity for a cell surface receptor of motor neurons (also known as efferent or effector neurons). Neurotoxin includes Clostridial toxins, preferably Clostridial botulinum toxins, both as non-complexed toxin (having a molecular weight of about 150 kDa) and as complexed with one or more non-toxin, toxin associated proteins; the complexes having molecular weights of about 900 kD, 700, kD, 500 kD or 300 kD, for example. Botulinum toxins can include toxins that are recombinantly made and modified in accordance with known molecular techniques, that is, a modified neurotoxin means a neurotoxin which has had one or more of its amino acids deleted, modified or replaced (as compared to the native neurotoxin) and includes neurotoxins made by recombinant technology as well as variants and fragments of a native or recombinantly produced neurotoxin.

As used herein "treating" or "to treat" means to alleviate, modulate, or eliminate either a symptom of a condition or disorder or the condition or disorder itself.

As used herein "local administration" or "locally administering" means direct administration of a pharmaceutical at, or to the vicinity of, a site on or within an animal body, at which site a biological effect of the pharmaceutical is desired. One example of local administration can include direct injection of a botulinum toxin. Topical administration as utilized herein is a type of local administration in which a pharmaceutical agent is administered to a person's periclitoral area, such as for example to the periclitoral area to which botulinum toxin, for example, is to be administered in accordance with the teachings presented herein.

As used herein "therapeutically effective" means an amount of toxin administered that will reduce or ameliorate a condition or symptom (in frequency and/or intensity) in a subject. The therapeutically effective amount of toxin, such as a botulinum neurotoxin, delivered to a subject, is an amount that achieves a desired effect yet does not result in undesirable systemic side effects associated with systemic neurotoxin poisoning, as known by those of ordinary skill in the art.

The combination of botulinum toxins and TEMs allows for dose reduction of active agents (with associated reduction in side effects) as well as possible synergistic effects. Non-paralytic effects, and also possible prophylactic effects especially when used early in the condition can provide further benefits.

Clostridial toxins are released by Clostridial bacterium as complexes comprising the approximately 150-kDa Clostridial toxin along with associated non-toxin proteins (NAPs). Identified NAPs include proteins possessing hemagglutination activity, such, e.g., a hemagglutinin of approximately 17-kDa (HA-17), a hemagglutinin of approximately 33-kDa (HA-33) and a hemagglutinin of approximately 70-kDa (HA-70); as well as non-toxic non-hemagglutinin (NTNH), a protein of approximately 130-kDa. Thus, the botulinum toxin type A complex can be produced by Clostridial bacterium as 900-kDa, 500-kDa and 300-kDa forms. Botulinum toxin types B and $C_1$ are apparently produced as only a 500-kDa complex. Botulinum toxin type D is produced as both 300-kDa and 500-kDa complexes. Finally, botulinum toxin types E and F are produced as only approximately 300-kDa complexes. The differences in molecular weight for the complexes are due to differing ratios of NAPs. The toxin complex is important for the intoxication process because it provides protection from adverse environmental conditions, resistance to protease digestion, and appears to facilitate internalization and activation of the toxin.

Figure 1B:
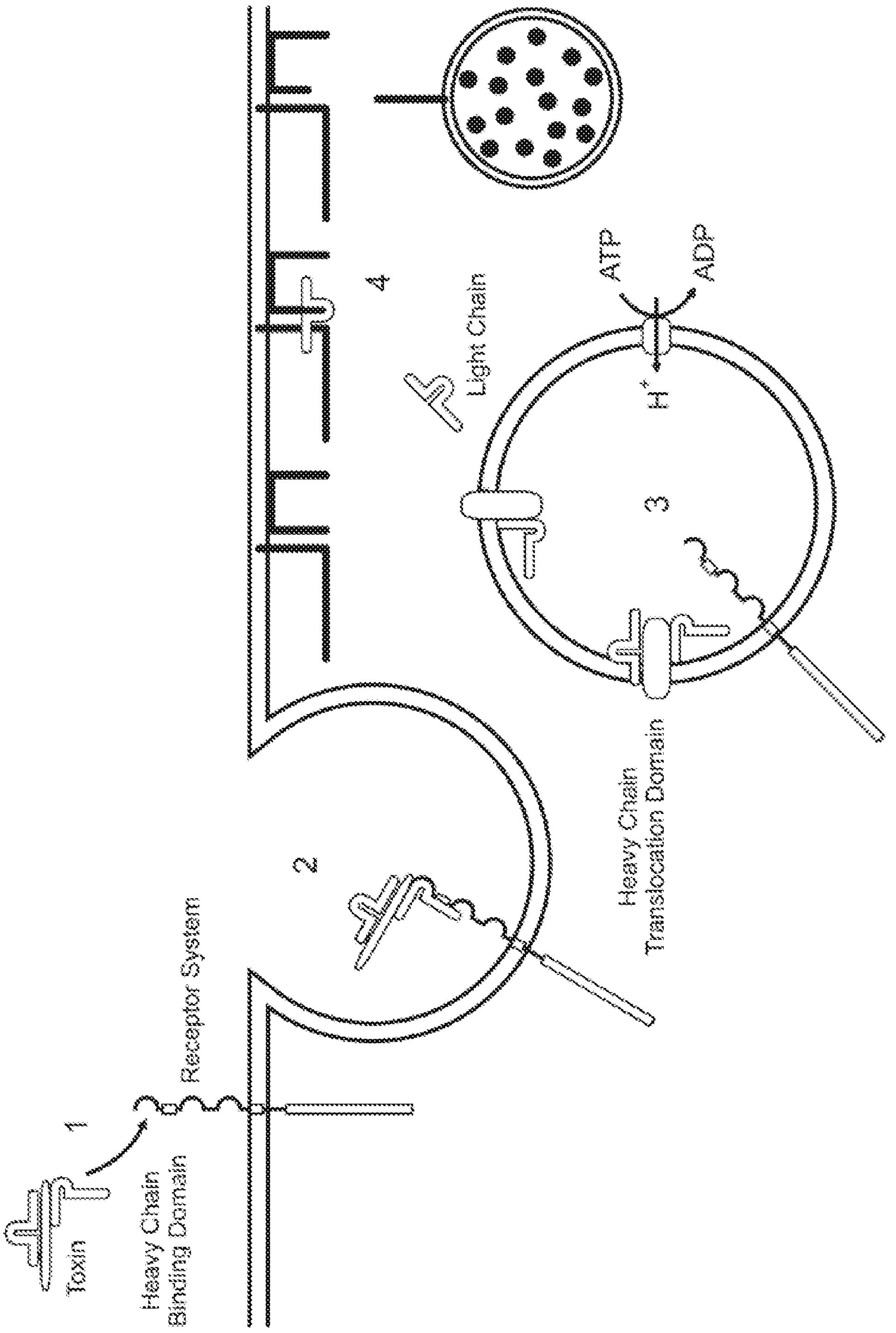
FIG. 1B shows a schematic of the intoxication mechanism for tetanus and botulinum toxin activity in a central and peripheral neuron. This intoxication process can be described as comprising four steps: 1) receptor binding, where a Clostridial toxin binds to a Clostridial receptor system and initiates the intoxication process; 2) complex internalization, where after toxin binding, a vesicle containing the toxin/receptor system complex is endocytosed into the cell; 3) light chain translocation, where multiple events are thought to occur, including, e.g., changes in the internal pH of the vesicle, formation of a channel pore comprising the HN domain of the Clostridial toxin heavy chain, separation of the Clostridial toxin light chain from the heavy chain, and release of the active light chain and 4) enzymatic target modification, where the activate light chain of Clostridial toxin proteolytically cleaves its target SNARE substrate, such as, e.g., SNAP-25, VAMP or Syntaxin, thereby preventing vesicle docking and neurotransmitter release.

A Clostridial toxin itself is translated as a single chain polypeptide that is subsequently cleaved by proteolytic scission within a disulfide loop by a naturally-occurring protease (FIG. 1). This cleavage occurs within the discrete di-chain loop region created between two cysteine residues that form a disulfide bridge. This post-translational processing yields a di-chain molecule comprising an approximately 50 kDa light chain (LC) and an approximately 100 kDa heavy chain (HC) held together by the single disulfide bond and non-covalent interactions between the two chains. The naturally-occurring protease used to convert the single chain molecule into the di-chain is currently not known. In some serotypes, such as, e.g., BoNT/A, the naturally-occurring protease is produced endogenously by the bacteria serotype and cleavage occurs within the cell before the toxin is release into the environment. However, in other serotypes, such as, e.g., BoNT/E, the bacterial strain appears not to produce an endogenous protease capable of converting the single chain form of the toxin into the di-chain form. In these situations, the toxin is released from the cell as a single-chain toxin which is subsequently converted into the di-chain form by a naturally-occurring protease found in the environment.

Each mature di-chain molecule of a Clostridial toxin comprises three functionally distinct domains: 1) an enzymatic domain located in the light chain (LC) that includes a metalloprotease region containing a zinc-dependent endopeptidase activity which specifically targets core components of the neurotransmitter release apparatus; 2) a translocation domain contained within the amino-terminal half of the heavy chain ($H_N$) that facilitates release of the LC from intracellular vesicles into the cytoplasm of the target cell; and 3) a binding domain found within the carboxyl-terminal half of the heavy chain ($H_C$) that determines the binding activity and binding specificity of the toxin to the receptor complex located at the surface of the target cell. The $H_C$ domain comprises two distinct structural features of roughly equal size that indicate function and are designated the $H_{CN}$ and $H_{CC}$ subdomains.

Clostridial toxins act on the nervous system by blocking the release of acetylcholine (ACh) at the pre-synaptic neuromuscular junction. The binding, translocation and enzymatic activity of these three functional domains are all necessary for toxicity. While all details of this process are not yet precisely known, the overall cellular intoxication mechanism whereby Clostridial toxins enter a neuron and inhibit neurotransmitter release is similar, regardless of serotype or subtype. Although applicants have no wish to be limited by the following description, the intoxication mechanism can be described as comprising at least four steps: 1) receptor binding, 2) complex internalization, 3) light chain translocation, and 4) enzymatic target modification (FIG. 1). The process is initiated when the binding domain of a Clostridial toxin binds to a toxin-specific receptor system located on the plasma membrane surface of a target cell. The binding specificity of a receptor complex is thought to be achieved, in part, by specific combinations of gangliosides and protein receptors that appear to distinctly comprise each Clostridial toxin receptor complex. Once bound, the toxin/receptor complexes are internalized by endocytosis and the internalized vesicles are sorted to specific intracellular routes. The translocation step appears to be triggered by the acidification of the vesicle compartment. This process seems to initiate pH-dependent structural rearrangements that increase hydrophobicity, create a pore in the vesicle membrane, and promote formation of the di-chain form of the toxin. Once di-chain formation occurs, light chain endopeptidase of the toxin is released from the intracellular vesicle via the pore into the cytosol where it appears to specifically target one of three known core components of the neurotransmitter release apparatus. These core proteins, vesicle-associated membrane protein (VAMP)/synaptobrevin, synaptosomal-associated protein of 25 kDa (SNAP-25) and Syntaxin, are necessary for synaptic vesicle docking and fusion at the nerve terminal and constitute members of the soluble N-ethylmaleimide-sensitive factor-attachment protein-receptor (SNARE) family. BoNT/A and BoNT/E cleave SNAP-25 in the carboxyl-terminal region, releasing a nine or twenty-six amino acid segment, respectively, and BoNT/C1 also cleaves SNAP-25 near the carboxyl-terminus. The botulinum serotypes BoNT/B, BoNT/D, BoNT/F and BoNT/G, and tetanus toxin, act on the conserved central portion of VAMP, and release the amino-terminal portion of VAMP into the cytosol. BoNT/C1 cleaves syntaxin at a single site near the cytosolic membrane surface.

Aspects of the present specification disclose, in part, in part, a Clostridial toxin. As used herein, the term "Clostridial toxin" refers to any toxin produced by a Clostridial toxin strain that can execute the overall cellular mechanism whereby a Clostridial toxin intoxicates a cell and encompasses the binding of a Clostridial toxin to a low or high affinity Clostridial toxin receptor, the internalization of the toxin/receptor complex, the translocation of the Clostridial toxin light chain into the cytoplasm and the enzymatic modification of a Clostridial toxin substrate. Non-limiting examples of Clostridial toxins include a Botulinum toxin like BoNT/A, a BoNT/B, a BoNT/$C_1$, a BoNT/D, a BoNT/E, a BoNT/F, a BoNT/G, a Tetanus toxin (TeNT), a *Baratii* toxin (BaNT), and a *Butyricum* toxin (BuNT). The BoNT/$C_2$ cytotoxin and BoNT/$C_3$ cytotoxin, not being neurotoxins, are excluded from the term "Clostridial toxin." A Clostridial toxin disclosed herein includes, without limitation, naturally occurring Clostridial toxin variants, such as, e.g., Clostridial toxin isoforms and Clostridial toxin subtypes; non-naturally occurring Clostridial toxin variants, such as, e.g., conservative Clostridial toxin variants, non-conservative Clostridial toxin variants, Clostridial toxin chimeric variants and active Clostridial toxin fragments thereof, or any combination thereof.

A Clostridial toxin disclosed herein also includes a Clostridial toxin complex. As used herein, the term "Clostridial toxin complex" refers to a complex comprising a Clostridial toxin and non-toxin associated proteins (NAPs), such as, e.g., a Botulinum toxin complex, a Tetanus toxin complex, a *Baratii* toxin complex, and a *Butyricum* toxin complex. Non-limiting examples of Clostridial toxin complexes include those produced by a *Clostridium botulinum*, such as, e.g., a 900-kDa BoNT/A complex, a 500-kDa BoNT/A complex, a 300-kDa BoNT/A complex, a 500-kDa BoNT/B complex, a 500-kDa BoNT/$C_1$ complex, a 500-kDa BoNT/D complex, a 300-kDa BoNT/D complex, a 300-kDa BoNT/E complex, and a 300-kDa BoNT/F complex.

Clostridial toxins can be produced using standard purification or recombinant biology techniques known to those skilled in the art. See, e.g., Hui Xiang et al., Animal Product Free System and Process for Purifying a Botulinum Toxin, U.S. Pat. No. 7,354,740, which is hereby incorporated by reference in its entirety. For example, a BoNT/A complex can be isolated and purified from an anaerobic fermentation by cultivating *Clostridium botulinum* type A in a suitable medium. Raw toxin can be harvested by precipitation with sulfuric acid and concentrated by ultramicrofiltration. Purification can be carried out by dissolving the acid precipitate in calcium chloride. The toxin can then be precipitated with cold ethanol. The precipitate can be dissolved in sodium phosphate buffer and centrifuged. Upon drying there can then be obtained approximately 900 kD crystalline BoNT/A complex with a specific potency of $3\times10^7$ $LD_{50}$ U/mg or greater. Furthermore, NAPs can be separated out to obtain purified toxin, such as e.g., BoNT/A with an approximately 150 kD molecular weight with a specific potency of 1-$2\times10^8$ $LD_{50}$ U/mg or greater, purified BoNT/B with an approximately 156 kD molecular weight with a specific potency of 1-$2\times10^8$ $LD_{50}$ U/mg or greater, and purified BoNT/F with an approximately 155 kD molecular weight with a specific potency of 1-$2\times10^7$ $LD_{50}$ U/mg or greater. See Edward J. Schantz & Eric A. Johnson, *Properties and use of Botulinum Toxin and Other Microbial Neurotoxins in Medicine*, Microbiol Rev. 56: 80-99 (1992), which is hereby incorporated in its entirety. As another example, recombinant Clostridial toxins can be recombinantly produced as described in Steward et al., Optimizing Expression of Active Botulinum Toxin Type A, U.S. Patent Publication 2008/0057575; and Steward et al., Optimizing Expression of Active Botulinum Toxin Type E, U.S. Patent Publication 2008/0138893, each of which is hereby incorporated in its entirety.

Clostridial toxins are also commercially available as pharmaceutical compositions include, BoNT/A preparations, such as, e.g., BOTOX® (Allergan, Inc., Irvine, Calif.), DYSPORT®/RELOXIN®, (Beaufour Ipsen, Porton Down, England), NEURONOX® (Medy-Tox, Inc., Ochang-myeon, South Korea), BTX-A (Lanzhou Institute Biological Products, China) and XEOMIN® (Merz Pharmaceuticals, GmbH., Frankfurt, Germany); and BoNT/B preparations, such as, e.g., MYOBLOC™/NEUROBLOC™ (Solstice Neurosciences, Inc., South San Francisco, Calif.). Clostridial toxin complexes may be obtained from, e.g., List Biological Laboratories, Inc. (Campbell, Calif.), the Centre for Applied Microbiology and Research (Porton Down, U.K), Wako (Osaka, Japan), and Sigma Chemicals (St Louis, Mo.).

In an embodiment, a Clostridial may be a Botulinum toxin, Tetanus toxin, a *Baratii* toxin, or a *Butyricum* toxin. In aspects of this embodiment, a Botulinum toxin may be a BoNT/A, a BoNT/B, a BoNT/$C_1$, a BoNT/D, a BoNT/E, a BoNT/F, or a BoNT/G. In another embodiment, a Clostridial toxin may be a Clostridial toxin variant. In aspects of this embodiment, a Clostridial toxin variant may be a naturally-occurring Clostridial toxin variant or a non-naturally-occurring Clostridial toxin variant. In other aspects of this embodiment, a Clostridial toxin variant may be a BoNT/A variant, a BoNT/B variant, a BoNT/$C_1$ variant, a BoNT/D variant, a BoNT/E variant, a BoNT/F variant, a BoNT/G variant, a TeNT variant, a BaNT variant, or a BuNT variant, where the variant is either a naturally-occurring variant or a non-naturally-occurring variant.

In an embodiment, a Clostridial toxin may be a Clostridial toxin complex. In aspects of this embodiment, a Clostridial toxin complex may be a BoNT/A complex, a BoNT/B complex, a BoNT/$C_1$ complex, a BoNT/D complex, a BoNT/E complex, a BoNT/F complex, a BoNT/G complex, a TeNT complex, a BaNT complex, or a BuNT complex. In other aspects of this embodiment, a Clostridial toxin complex may be a 900-kDa BoNT/A complex, a 500-kDa BoNT/A complex, a 300-kDa BoNT/A complex, a 500-kDa BoNT/B complex, a 500-kDa BoNT/C1 complex, a 500-kDa BoNT/D complex, a 300-kDa BoNT/D complex, a 300-kDa BoNT/E complex, or a 300-kDa BoNT/F complex.

Aspects of the present disclosure comprise, in part, a Targeted Exocytosis Modulator. As used herein, the term "Targeted Exocytosis Modulator" is synonymous with "TEM" or "retargeted endopeptidase." Generally, a TEM comprises an enzymatic domain from a Clostridial toxin light chain, a translocation domain from a Clostridial toxin heavy chain, and a targeting domain. The targeting domain of a TEM provides an altered cell targeting capability that targets the molecule to a receptor other than the native Clostridial toxin receptor utilized by a naturally-occurring Clostridial toxin. This re-targeted capability is achieved by replacing the naturally-occurring binding domain of a Clostridial toxin with a targeting domain having a binding activity for a non-Clostridial toxin receptor. Although binding to a non-Clostridial toxin receptor, a TEM undergoes all the other steps of the intoxication process including internalization of the TEM/receptor complex into the cytoplasm, formation of the pore in the vesicle membrane and di-chain molecule, translocation of the enzymatic domain into the cytoplasm, and exerting a proteolytic effect on a component of the SNARE complex of the target cell.

However, an important difference between TEMs, such as, e.g., TEMs disclosed herein, and native Clostridial toxins is that since TEMs do not target motor neurons, the lethality associated with over-dosing an individual with a TEM is greatly minimized, if not avoided altogether. For example, a TEM comprising an opioid targeting domain can be administered at 10,000 times the therapeutically effective dose before evidence of lethality is observed, and this lethality is due to the passive diffusion of the molecule and not via the intoxication process. Thus, for all practical purposes TEMs are non-lethal molecules.

As used herein, the term "Clostridial toxin enzymatic domain" refers to a Clostridial toxin polypeptide located in the light chain of a Clostridial toxin that executes the enzymatic target modification step of the intoxication process. A Clostridial toxin enzymatic domain includes a metalloprotease region containing a zinc-dependent endopeptidase activity which specifically targets core components of the neurotransmitter release apparatus. Thus, a Clostridial toxin enzymatic domain specifically targets and proteolytically cleavages of a Clostridial toxin substrate, such as, e.g., SNARE proteins like a SNAP-25 substrate, a VAMP substrate and a Syntaxin substrate.

A Clostridial toxin enzymatic domain includes, without limitation, naturally occurring Clostridial toxin enzymatic domain variants, such as, e.g., Clostridial toxin enzymatic domain isoforms and Clostridial toxin enzymatic domain subtypes; non-naturally occurring Clostridial toxin enzymatic domain variants, such as, e.g., conservative Clostridial toxin enzymatic domain variants, non-conservative Clostridial toxin enzymatic domain variants, Clostridial toxin enzymatic domain chimeras, active Clostridial toxin enzymatic domain fragments thereof, or any combination thereof. Non-limiting examples of a Clostridial toxin enzymatic domain include, e.g., a BoNT/A enzymatic domain, a BoNT/B enzymatic domain, a BoNT/C1 enzymatic domain, a BoNT/D enzymatic domain, a BoNT/E enzymatic domain, a BoNT/F enzymatic domain, a BoNT/G enzymatic domain, a TeNT enzymatic domain, a BaNT enzymatic domain, and a BuNT enzymatic domain.

As used herein, the term "Clostridial toxin translocation domain" refers to a Clostridial toxin polypeptide located within the amino-terminal half of the heavy chain of a Clostridial toxin that executes the translocation step of the intoxication process. The translocation step appears to involve an allosteric conformational change of the translocation domain caused by a decrease in pH within the intracellular vesicle. This conformational change results in the formation of a pore in the vesicular membrane that permits the movement of the light chain from within the vesicle into the cytoplasm. Thus, a Clostridial toxin translocation domain facilitates the movement of a Clostridial toxin light chain across a membrane of an intracellular vesicle into the cytoplasm of a cell.

A Clostridial toxin translocation domain includes, without limitation, naturally occurring Clostridial toxin translocation domain variants, such as, e.g., Clostridial toxin translocation domain isoforms and Clostridial toxin translocation domain subtypes; non-naturally occurring Clostridial toxin translocation domain variants, such as, e.g., conservative Clostridial toxin translocation domain variants, non-conservative Clostridial toxin translocation domain variants, Clostridial toxin translocation domain chimerics, active Clostridial toxin translocation domain fragments thereof, or any combination thereof. Non-limiting examples of a Clostridial toxin translocation domain include, e.g., a BoNT/A translocation domain, a BoNT/B translocation domain, a BoNT/C1 translocation domain, a BoNT/D translocation domain, a BoNT/E translocation domain, a BoNT/F translocation domain, a BoNT/G translocation domain, a TeNT translocation domain, a BaNT translocation domain, and a BuNT translocation domain.

As used herein, the term "targeting domain" is synonymous with "binding domain" or "targeting moiety" and refers to a polypeptide that executes the receptor binding and/or complex internalization steps of the intoxication process, with the proviso that the binding domain is not a Clostridial toxin binding domain found within the carboxyl-terminal half of the heavy chain of a Clostridial toxin. A targeting domain includes a receptor binding region that confers the binding activity and/or specificity of the targeting domain for its cognate receptor. As used herein, the term "cognate receptor" refers to a receptor for which the targeting domain preferentially interacts with under physiological conditions, or under in vitro conditions substantially approximating physiological conditions. As used herein, the term "preferentially interacts" is synonymous with "preferentially binding" and refers to an interaction that is statistically significantly greater in degree relative to a control. With reference to a targeting domain disclosed herein, a targeting domain binds to its cognate receptor to a statistically significantly greater degree relative to a non-cognate receptor. Said another way, there is a discriminatory binding of the targeting domain to its cognate receptor relative to a non-cognate receptor. Thus, a targeting domain directs binding to a TEM-specific receptor located on the plasma membrane surface of a target cell.

In an embodiment, a targeting domain disclosed herein has an association rate constant that confers preferential binding to its cognate receptor. In aspects of this embodiment, a targeting domain disclosed herein binds to its cognate receptor with an association rate constant of, e.g., less than $1\times10^5$ $M^{-1}$ $s^{-1}$, less than $1\times10^6$ $M^{-1}$ $s^{-1}$, less than $1\times10^7$ $M^{-1}$ $s^{-1}$, or less than $1\times10^8$ $M^{-1}$ $s^{-1}$. In other aspects of this embodiment, a targeting domain disclosed herein binds to its cognate receptor with an association rate constant of, e.g., more than $1\times10^5$ $M^{-1}$ $s^{-1}$, more than $1\times10^6$ $M^{-1}$ $s^{-1}$, more than $1\times10^7$ $M^{-1}$ $s^{-1}$, or more than $1\times10^8$ $M^{-1}$ $s^{-1}$. In yet other aspects of this embodiment, a targeting domain disclosed herein binds to its cognate receptor with an association rate constant between $1\times10^5$ $M^{-1}$ $s^{-1}$ to $1\times10^8$ $M^{-1}$ $s^{-1}$, $1\times10^6$ $M^{-1}$ $s^{-1}$ to $1\times10^8$ $M^{-1}$ $s^{-1}$, $1\times10^5$ $M^{-1}$ $s^{-1}$ to $1\times10^7$ $M^{-1}$ $s^{-1}$, or $1\times10^6$ $M^{-1}$ $s^{-1}$ to $1\times10^7$ $M^{-1}$ $s^{-1}$.

In another embodiment, a targeting domain disclosed herein has an association rate constant that is greater for its cognate target receptor relative to a non-cognate receptor. In other aspects of this embodiment, a targeting domain disclosed herein has an association rate constant that is greater for its cognate target receptor relative to a non-cognate receptor by, at least one-fold, at least two-fold, at least three-fold, at least four fold, at least five-fold, at least 10 fold, at least 50 fold, at least 100 fold, at least 1000 fold, at least 10,000 fold, or at least 100,000 fold. In other aspects of this embodiment, a targeting domain disclosed herein has an association rate constant that is greater for its cognate target receptor relative to a non-cognate receptor by, e.g., about one-fold to about three-fold, about one-fold to about five-fold, about one-fold to about 10-fold, about one-fold to about 100-fold, about one-fold to about 1000-fold, about five-fold to about 10-fold, about five-fold to about 100-fold, about five-fold to about 1000-fold, about 10-fold to about 100-fold, about 10-fold to about 1000-fold, about 10-fold to about 10,000-fold, or about 10-fold to about 100,000-fold.

In yet another embodiment, a targeting domain disclosed herein has a disassociation rate constant that confers preferential binding to its cognate receptor. In other aspects of this embodiment, a targeting domain disclosed herein binds to its cognate receptor with a disassociation rate constant of less than $1\times10^{-3}$ $s^{-1}$, less than $1\times10^{-4}$ $s^{-1}$, or less than $1\times10^{-5}$ $s^{-1}$. In yet other aspects of this embodiment, a targeting domain disclosed herein binds to its cognate receptor with a disassociation rate constant of, e.g., less than $1.0\times10^{-4}$ $s^{-1}$, less than $2.0\times10^{-4}$ $s^{-1}$, less than $3.0\times10^{-4}$ $s^{-1}$, less than $4.0\times10^{-4}$ $s^{-1}$, less than $5.0\times10^{-4}$ $s^{-1}$, less than $6.0\times10^{-4}$ $s^{-1}$, less than $7.0\times10^{-4}$ $s^{-1}$, less than $8.0\times10^{-4}$ $s^{-1}$, or less than $9.0\times10^{-4}$ $s^{-1}$. In still other aspects of this embodiment, a targeting domain disclosed herein binds to its cognate receptor with a disassociation rate constant of, e.g., more than $1\times10^{-3}$ $s^{-1}$, more than $1\times10^{-4}$ $s^{-1}$, or more than $1\times10^{-5}$ $s^{-1}$. In other aspects of this embodiment, a targeting domain disclosed herein binds to its cognate receptor with a disassociation rate constant of, e.g., more than $1.0\times10^{-4}$ $s^{-1}$, more than $2.0\times10^{-4}$ $s^{-1}$, more than $3.0\times10^{-4}$ $s^{-1}$, more than $4.0\times10^{-4}$ $s^{-1}$, more than $5.0\times10^{-4}$ $s^{-1}$, more than $6.0\times10^{-1}$ $s^{-1}$, more than $7.0\times10^{-4}$ $s^{-1}$, more than $8.0\times10^{-4}$ $s^{-1}$, or more than $9.0\times10^{-4}$ $s^{-1}$.

In still another embodiment, a targeting domain disclosed herein has a disassociation rate constant that is less for its cognate target receptor relative to a non-cognate receptor. In other aspects of this embodiment, a targeting domain disclosed herein has a disassociation rate constant that is less for its cognate target receptor relative to a non-cognate receptor by, e.g., at least one-fold, at least two-fold, at least three-fold, at least four fold, at least five-fold, at least 10 fold, at least 50 fold, at least 100 fold, at least 1000 fold, at least 10,000 fold, or at least 100,000 fold. In other aspects of this embodiment, a targeting domain disclosed herein has a disassociation rate constant that is less for its cognate target receptor relative to a non-cognate receptor by, e.g., about one-fold to about three-fold, about one-fold to about five-fold, about one-fold to about 10-fold, about one-fold to about 100-fold, about one-fold to about 1000-fold, about five-fold to about 10-fold, about five-fold to about 100-fold, about five-fold to about 1000-fold, about 10-fold to about 100-fold, about 10-fold to about 1000-fold, about 10-fold to about 10,000-fold, or about 10-fold to about 100,000-fold.

In another embodiment, a targeting domain disclosed herein has an equilibrium disassociation constant that confers preferential binding to its cognate receptor. In other aspects of this embodiment, a targeting domain disclosed herein binds to its cognate receptor with an equilibrium disassociation constant of, e.g., less than 0.500 nM. In yet other aspects of this embodiment, a targeting domain disclosed herein binds to its cognate receptor with an equilibrium disassociation constant of, e.g., less than 0.500 nM, less than 0.450 nM, less than 0.400 nM, less than 0.350 nM, less than 0.300 nM, less than 0.250 nM, less than 0.200 nM, less than 0.150 nM, less than 0.100 nM, or less than 0.050 nM. In other aspects of this embodiment, a targeting domain disclosed herein binds to its cognate receptor with an equilibrium disassociation constant of, e.g., more than 0.500 nM, more than 0.450 nM, more than 0.400 nM, more than 0.350 nM, more than 0.300 nM, more than 0.250 nM, more than 0.200 nM, more than 0.150 nM, more than 0.100 nM, or more than 0.050 nM.

In yet another embodiment, a targeting domain disclosed herein has an equilibrium disassociation constant that is greater for its cognate target receptor relative to a non-cognate receptor. In other aspects of this embodiment, a targeting domain disclosed herein has an equilibrium disassociation constant that is greater for its cognate target receptor relative to a non-cognate receptor by, e.g., at least one-fold, at least two-fold, at least three-fold, at least four fold, at least five-fold, at least 10 fold, at least 50 fold, at least 100 fold, at least 1000 fold, at least 10,000 fold, or at least 100,000 fold. In other aspects of this embodiment, a targeting domain disclosed herein has an equilibrium disassociation constant that is greater for its cognate target receptor relative to a non-cognate receptor by, e.g., about one-fold to about three-fold, about one-fold to about five-fold, about one-fold to about 10-fold, about one-fold to about 100-fold, about one-fold to about 1000-fold, about five-fold to about 10-fold, about five-fold to about 100-fold, about five-fold to about 1000-fold, about 10-fold to about 100-fold, about 10-fold to about 1000-fold, about 10-fold to about 10,000-fold, or about 10-fold to about 100,000-fold.

In another embodiment, a targeting domain disclosed herein may be one that preferentially interacts with a receptor located on a sensory neuron. In an aspect of this embodiment, the sensory neuron targeting domain is one whose cognate receptor is located exclusively on the plasma membrane of sensory neurons. In another aspect of this embodiment, the sensory neuron targeting domain is one whose cognate receptor is located primarily on the plasma membrane of sensory neuron. For example, a receptor for a sensory neuron targeting domain is located primarily on a sensory neuron when, e.g., at least 60% of all cells that have a cognate receptor for a sensory neuron targeting domain on the surface of the plasma membrane are sensory neurons, at least 70% of all cells that have a cognate receptor for a sensory neuron targeting domain on the surface of the plasma membrane are sensory neurons, at least 80% of all cells that have a cognate receptor for a sensory neuron targeting domain on the surface of the plasma membrane are sensory neurons, or at least 90% of all cells that have a cognate receptor for a sensory neuron targeting domain on the surface of the plasma membrane are sensory neurons. In yet another aspect of this embodiment, the sensory neuron targeting domain is one whose cognate receptor is located on the plasma membrane of several types of cells, including sensory neurons. In still another aspect of this embodiment, the sensory neuron targeting domain is one whose cognate receptor is located on the plasma membrane of several types of cells, including sensory neurons, with the proviso that motor neurons are not one of the other types of cells.

In another embodiment, a targeting domain disclosed herein may be one that preferentially interacts with a receptor located on a sympathetic neuron. In an aspect of this embodiment, the sympathetic neuron targeting domain is one whose cognate receptor is located exclusively on the plasma membrane of sympathetic neurons. In another aspect of this embodiment, the sympathetic neuron targeting domain is one whose cognate receptor is located primarily on the plasma membrane of sympathetic neuron. For example, a receptor for a sympathetic neuron targeting domain is located primarily on a sympathetic neuron when, e.g., at least 60% of all cells that have a cognate receptor for a sympathetic neuron targeting domain on the surface of the plasma membrane are sympathetic neurons, at least 70% of all cells that have a cognate receptor for a sympathetic neuron targeting domain on the surface of the plasma membrane are sympathetic neurons, at least 80% of all cells that have a cognate receptor for a sympathetic neuron targeting domain on the surface of the plasma membrane are sympathetic neurons, or at least 90% of all cells that have a cognate receptor for a sympathetic neuron targeting domain on the surface of the plasma membrane are sympathetic neurons. In yet another aspect of this embodiment, the sympathetic neuron targeting domain is one whose cognate receptor is located on the plasma membrane of several types of cells, including sympathetic neurons. In still another aspect of this embodiment, the sympathetic neuron targeting domain is one whose cognate receptor is located on the plasma membrane of several types of cells, including sympathetic neurons, with the proviso that motor neurons are not one of the other types of cells.

In another embodiment, a targeting domain disclosed herein may be one that preferentially interacts with a receptor located on a parasympathetic neuron. In an aspect of this embodiment, the parasympathetic neuron targeting domain is one whose cognate receptor is located exclusively on the plasma membrane of parasympathetic neurons. In another aspect of this embodiment, the parasympathetic neuron targeting domain is one whose cognate receptor is located primarily on the plasma membrane of parasympathetic neuron. For example, a receptor for a parasympathetic neuron targeting domain is located primarily on a parasympathetic neuron when, e.g., at least 60% of all cells that have a cognate receptor for a parasympathetic neuron targeting domain on the surface of the plasma membrane are parasympathetic neurons, at least 70% of all cells that have a cognate receptor for a parasympathetic neuron targeting domain on the surface of the plasma membrane are parasympathetic neurons, at least 80% of all cells that have a cognate receptor for a parasympathetic neuron targeting domain on the surface of the plasma membrane are parasympathetic neurons, or at least 90% of all cells that have a cognate receptor for a parasympathetic neuron targeting domain on the surface of the plasma membrane are parasympathetic neurons. In yet another aspect of this embodiment, the parasympathetic neuron targeting domain is one whose cognate receptor is located on the plasma membrane of several types of cells, including parasympathetic neurons. In still another aspect of this embodiment, the parasympathetic neuron targeting domain is one whose cognate receptor is located on the plasma membrane of several types of cells, including parasympathetic neurons, with the proviso that motor neurons are not one of the other types of cells.

In another embodiment, a targeting domain disclosed herein is an opioid peptide targeting domain, a galanin peptide targeting domain, a PAR peptide targeting domain, a somatostatin peptide targeting domain, a neurotensin peptide targeting domain, a SLURP peptide targeting domain, an angiotensin peptide targeting domain, a tachykinin peptide targeting domain, a Neuropeptide Y related peptide targeting domain, a kinin peptide targeting domain, a melanocortin peptide targeting domain, or a granin peptide targeting domain, a glucagon like hormone peptide targeting domain, a secretin peptide targeting domain, a pituitary adenylate cyclase activating peptide (PACAP) peptide targeting domain, a growth hormone-releasing hormone (GHRH) peptide targeting domain, a vasoactive intestinal peptide (VIP) peptide targeting domain, a gastric inhibitory peptide (GIP) peptide targeting domain, a calcitonin peptide targeting domain, a visceral gut peptide targeting domain, a neurotrophin peptide targeting domain, a head activator (HA) peptide, a glial cell line-derived neurotrophic factor (GDNF) family of ligands (GFL) peptide targeting domain, a RF-amide related peptide (RFRP) peptide targeting domain, a neurohormone peptide targeting domain, or a neuroregulatory cytokine peptide targeting domain, an interleukin (IL) targeting domain, vascular endothelial growth factor (VEGF) targeting domain, an insulin-like growth factor (IGF) targeting domain, an epidermal growth factor (EGF) targeting domain, a Transformation Growth Factor-β (TGFβ) targeting domain, a Bone Morphogenetic Protein (BMP) targeting domain, a Growth and Differentiation Factor (GDF) targeting domain, an activin targeting domain, or a Fibroblast Growth Factor (FGF) targeting domain, or a Platelet-Derived Growth Factor (PDGF) targeting domain.

In an aspect of this embodiment, an opioid peptide targeting domain is an enkephalin peptide, a bovine adrenomedullary-22 (BAM22) peptide, an endomorphin peptide, an endorphin peptide, a dynorphin peptide, a nociceptin peptide, or a hemorphin peptide. In another aspect of this embodiment, an enkephalin peptide targeting domain is a Leu-enkephalin peptide, a Met-enkephalin peptide, a Met-enkephalin MRGL peptide, or a Met-enkephalin MRF peptide. In another aspect of this embodiment, a bovine adrenomedullary-22 peptide targeting domain is a BAM22 (1-12) peptide, a BAM22 (6-22) peptide, a BAM22 (8-22) peptide, or a BAM22 (1-22) peptide. In another aspect of this embodiment, an endomorphin peptide targeting domain is an endomorphin-1 peptide or an endomorphin-2 peptide. In another aspect of this embodiment, an endorphin peptide targeting domain an endorphin-α peptide, a neoendorphin-α peptide, an endorphin-β peptide, a neoendorphin-β peptide, or an endorphin-γ peptide. In another aspect of this embodiment, a dynorphin peptide targeting domain is a dynorphin A peptide, a dynorphin B (leumorphin) peptide, or a rimorphin peptide. In another aspect of this embodiment, a nociceptin peptide targeting domain is a nociceptin RK peptide, a nociceptin peptide, a neuropeptide 1 peptide, a neuropeptide 2 peptide, or a neuropeptide 3 peptide. In another aspect of this embodiment, a hemorphin peptide targeting domain is a LVVH7 peptide, a VVH7 peptide, a VH7 peptide, a H7 peptide, a LVVH6 peptide, a LVVH5 peptide, a VVH5 peptide, a LVVH4 peptide, or a LVVH3 peptide.

In an aspect of this embodiment, a galanin peptide targeting domain is a galanin peptide, a galanin message-associated peptide (GMAP) peptide, a galanin like protein (GALP) peptide, or an alarin peptide.

In an aspect of this embodiment, a PAR peptide targeting domain is a PAR1 peptide, a PAR2 peptide, a PAR3 peptide and a PAR4 peptide. In an aspect of this embodiment, a somatostatin peptide targeting domain is a somatostatin peptide or a cortistatin peptide. In an aspect of this embodiment, a neurotensin peptide targeting domain a neurotensin or a neuromedin N. In an aspect of this embodiment, a SLURP peptide targeting domain is a SLURP-1 peptide or a SLURP-2 peptide. In an aspect of this embodiment, an angiotensin peptide targeting domain is an angiotensin peptide.

In an aspect of this embodiment, a tachykinin peptide targeting domain is a Substance P peptide, a neuropeptide K peptide, a neuropeptide gamma peptide, a neurokinin A peptide, a neurokinin B peptide, a hemokinin peptide, or a endokinin peptide. In an aspect of this embodiment, a Neuropeptide Y related peptide targeting domain is a Neuropeptide Y peptide, a Peptide YY peptide, Pancreatic peptide peptide, a Pancreatic icosapeptide peptide, a Pancreatic Hormone domain peptide, a CXCL12 peptide, and a Sjogren syndrome antigen B peptide. In an aspect of this embodiment, a kinin peptide targeting domain is a bradykinin peptide, a kallidin peptide, a desArg9 bradykinin peptide, a desArg10 bradykinin peptide, a kininogen peptide, gonadotropin releasing hormone 1 peptide, chemokine peptide, an arginine vasopressin peptide.

In an aspect of this embodiment, a melanocortin peptide targeting domain comprises a melanocyte stimulating hormone peptide, an adrenocorticotropin peptide, a lipotropin peptide, or a melanocortin peptide derived neuropeptide. In an aspect of this embodiment, a melanocyte stimulating hormone peptide targeting domain comprises an α-melanocyte stimulating hormone peptide, a β-melanocyte stimulating hormone peptide, or a γ-melanocyte stimulating hormone peptide. In an aspect of this embodiment, an adrenocorticotropin peptide targeting domain comprises an adrenocorticotropin or a Corticotropin-like intermediary peptide. In an aspect of this embodiment, a lipotropin peptide targeting domain comprises a β-lipotropin peptide or a γ-lipotropin peptide.

In an aspect of this embodiment, a granin peptide targeting domain comprises a chromogranin A peptide, a chromogranin B peptide, a chromogranin C (secretogranin II) peptide, a secretogranin IV peptide, or a secretogranin VI peptide. In an aspect of this embodiment, a chromogranin A peptide targeting domain comprises a β-granin peptide, a vasostatin peptide, a chromostatin peptide, a pancreastatin peptide, a WE-14 peptide, a catestatin peptide, a parastatin peptide, or a GE-25 peptide. In an aspect of this embodiment, a chromogranin B peptide targeting domain comprises a GAWK peptide, an adrenomedullary peptide, or a secretolytin peptide. In an aspect of this embodiment, a chromogranin C peptide targeting domain comprises a secretoneurin peptide.

In an aspect of this embodiment, a glucagons-like hormone peptide targeting domain is a glucagon-like peptide-1, a glucagon-like peptide-2, a glicentin, a glicentin-related peptide (GRPP), a glucagon, or an oxyntomodulin (OXY). In an aspect of this embodiment, a secretin peptide targeting domain is a secretin peptide. In an aspect of this embodiment, a pituitary adenylate cyclase activating peptide targeting domain is a pituitary adenylate cyclase activating peptide. In an aspect of this embodiment, a growth hormone-releasing hormone peptide targeting domain a growth hormone-releasing hormone peptide. In an aspect of this embodiment, a vasoactive intestinal peptide targeting domain is a vasoactive intestinal peptide-1 peptide or a vasoactive intestinal peptide-2 peptide. In an aspect of this embodiment, a gastric inhibitory peptide targeting domain is a gastric inhibitory peptide. In an aspect of this embodiment, a calcitonin peptide targeting domain is a calcitonin peptide, an amylin peptide, a calcitonin-related peptide α, a calcitonin-related peptide β, and a islet amyloid peptide. In an aspect of this embodiment, a visceral gut peptide targeting domain is a gastrin peptide, a gastrin-releasing peptide, or a cholecystokinin peptide.

In an aspect of this embodiment, a neurotrophin peptide targeting domain is a nerve growth factor (NGF) peptide, a brain derived neurotrophic factor (BDNF) peptide, a neurotrophin-3 (NT-3) peptide, a neurotrophin-4/5 (NT-4/5) peptide, or an amyloid beta (A4) precursor protein neurotrophin (APP) peptide. In an aspect of this embodiment, a head activator peptide targeting domain is a head activator peptide. In an aspect of this embodiment, a glial cell line-derived neurotrophic factor family of ligands peptide targeting domain is a glial cell line-derived neurotrophic factor peptide, a Neurturin peptide, a Persephin peptide, or an Artemin peptide. In an aspect of this embodiment, a RF-amide related peptide targeting domain a RF-amide related peptide-1, a RF-amide related peptide-2, a RF-amide related peptide-3, a neuropeptide AF, or a neuropeptide FF.

In an aspect of this embodiment, a neurohormone peptide targeting domain is a corticotropin-releasing hormone (CCRH), a parathyroid hormone (PTH), a parathyroid hormone-like hormone (PTHLH), a PHYH, a thyrotropin-releasing hormone (TRH), an urocortin-1 (UCN1), an urocortin-2 (UCN2), an urocortin-3 (UCN3), or an urotensin 2 (UTS2). In an aspect of this embodiment, a neuroregulatory cytokine peptide targeting domain is a ciliary neurotrophic factor peptide, a glycophorin-A peptide, a leukemia inhibitory factor peptide, a cardiotrophin-1 peptide, a cardiotrophin-like cytokine peptide, a neuroleukin peptide, and an onostatin M peptide. In an aspect of this embodiment, an IL peptide targeting domain is an IL-1 peptide, an IL-2 peptide, an IL-3 peptide, an IL-4 peptide, an IL-5 peptide, an IL-6 peptide, an IL-7 peptide, an IL-8 peptide, an IL-9 peptide, an IL-10 peptide, an IL-11 peptide, an IL-12 peptide, an IL-18 peptide, an IL-32 peptide, or an IL-33 peptide.

In an aspect of this embodiment, a VEGF peptide targeting domain is a VEGF-A peptide, a VEGF-B peptide, a VEGF-C peptide, a VEGF-D peptide, or a placenta growth factor (PIGF) peptide. In an aspect of this embodiment, an IGF peptide targeting domain is an IGF-1 peptide or an IGF-2 peptide. In an aspect of this embodiment, an EGF peptide targeting domain an EGF, a heparin-binding EGF-like growth factor (HB-EGF), a transforming growth factor-α (TGF-α), an amphiregulin (AR), an epiregulin (EPR), an epigen (EPG), a betacellulin (BTC), a neuregulin-1 (NRG1), a neuregulin-2 (NRG2), a neuregulin-3, (NRG3), or a neuregulin-4 (NRG4). In an aspect of this embodiment, a FGF peptide targeting domain is a FGF1 peptide, a FGF2 peptide, a FGF3 peptide, a FGF4 peptide, a FGF5 peptide, a FGF6 peptide, a FGF7 peptide, a FGF8 peptide, a FGF9 peptide, a FGF10 peptide, a FGF17 peptide, or a FGF18 peptide. In an aspect of this embodiment, a PDGF peptide targeting domain is a PDGFα peptide or a PDGFβ peptide.

In an aspect of this embodiment, a TGFβ peptide targeting domain is a TGFβ1 peptide, a TGFβ2 peptide, a TGFβ3 peptide, or a TGFβ4 peptide. In an aspect of this embodiment, a BMP peptide targeting domain is a BMP2 peptide, a BMP3 peptide, a BMP4 peptide, a BMP5 peptide, a BMP6 peptide, a BMP7 peptide, a BMP8 peptide, or a BMP10 peptide. In an aspect of this embodiment, a GDF peptide targeting domain is a GDF1 peptide, a GDF2 peptide, a GDF3 peptide, a GDF5 peptide, a GDF6 peptide, a GDF7 peptide, a GDF8 peptide, a GDF10 peptide, a GDF11 peptide, or a GDF15 peptide. In an aspect of this embodiment, an activin peptide targeting domain is an activin A peptide, an activin B peptide, an activin C peptide, an activin E peptide, or an inhibin A peptide.

Figure 2:
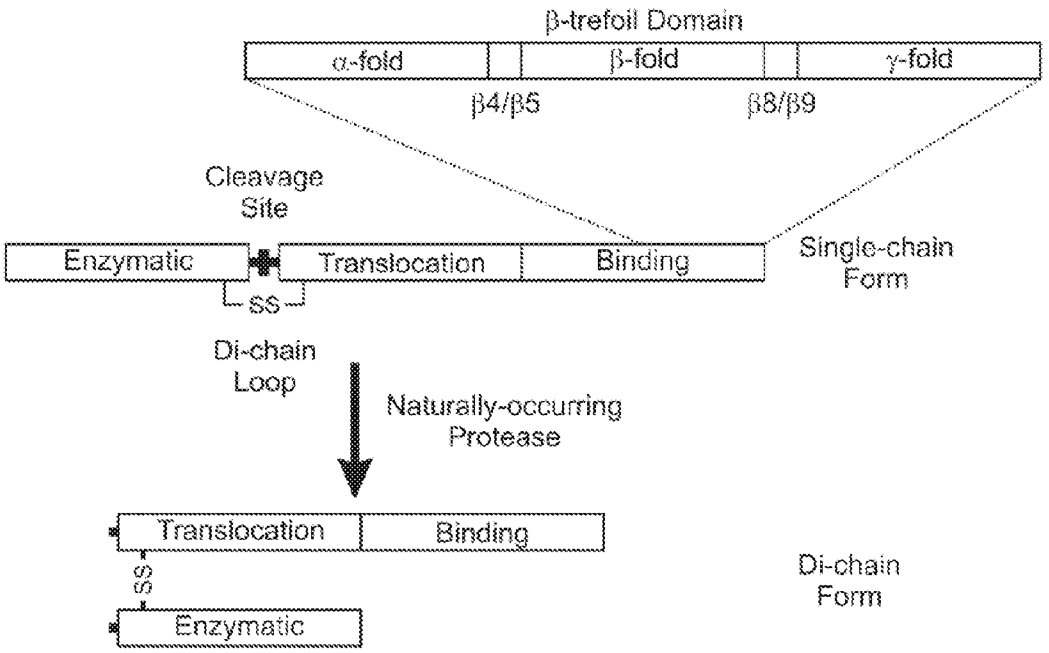
FIG. 2 shows the domain organization of naturally-occurring Clostridial toxins. The single-chain form depicts the amino to carboxyl linear organization comprising an enzymatic domain, a translocation domain, and a retargeted peptide binding domain. The di-chain loop region located between the translocation and enzymatic domains is depicted by the double SS bracket. This region comprises an endogenous di-chain loop protease cleavage site that upon proteolytic cleavage with a naturally-occurring protease, such as, e.g., an endogenous Clostridial toxin protease or a naturally-occurring protease produced in the environment, converts the single-chain form of the toxin into the di-chain form. Above the single-chain form, the $H_{CC}$ region of the Clostridial toxin binding domain is depicted. This region comprises the β-trefoil domain which comprises in an amino to carboxyl linear organization an α-fold, a β4/β5 hairpin turn, a β-fold, a β8/β9 hairpin turn and a γ-fold.

As discussed above, naturally-occurring Clostridial toxins are organized into three functional domains comprising a linear amino-to-carboxyl single polypeptide order of the enzymatic domain (amino region position), the translocation domain (middle region position) and the binding domain (carboxyl region position) (FIG. 2). This naturally-occurring order can be referred to as the carboxyl presentation of the binding domain because the domain necessary for binding to the receptor is located at the carboxyl region position of the Clostridial toxin. However, it has been shown that Clostridial toxins can be modified by rearranging the linear amino-to-carboxyl single polypeptide order of the three major domains and locating a targeting moiety at the amino region position of a Clostridial toxin, referred to as amino presentation, as well as in the middle region position, referred to as central presentation (FIG. 4).

Thus, a TEM can comprise a targeting domain in any and all locations with the proviso that TEM is capable of performing the intoxication process. Non-limiting examples include, locating a targeting domain at the amino terminus of a TEM; locating a targeting domain between a Clostridial toxin enzymatic domain and a Clostridial toxin translocation domain of a TEM; and locating a targeting domain at the carboxyl terminus of a TEM. Other non-limiting examples include, locating a targeting domain between a Clostridial toxin enzymatic domain and a Clostridial toxin translocation domain of a TEM. The enzymatic domain of naturally-occurring Clostridial toxins contains the native start methionine. Thus, in domain organizations where the enzymatic domain is not in the amino-terminal location an amino acid sequence comprising the start methionine should be placed in front of the amino-terminal domain. Likewise, where a targeting domain is in the amino-terminal position, an amino acid sequence comprising a start methionine and a protease cleavage site may be operably-linked in situations in which a targeting domain requires a free amino terminus, see, e.g., Shengwen Li et al., Degradable Clostridial Toxins, U.S. patent application Ser. No. 11/572,512 (Jan. 23, 2007), which is hereby incorporated by reference in its entirety. In addition, it is known in the art that when adding a polypeptide that is operably-linked to the amino terminus of another polypeptide comprising the start methionine that the original methionine residue can be deleted.

A TEM disclosed herein may optionally comprise an exogenous protease cleavage site that allows the use of an exogenous protease to convert the single-chain polypeptide form of a TEM into its more active di-chain form. As used herein, the term "exogenous protease cleavage site" is synonymous with a "non-naturally occurring protease cleavage site" or "non-native protease cleavage site" and means a protease cleavage site that is not naturally found in a di-chain loop region from a naturally occurring Clostridial toxin.

Naturally-occurring Clostridial toxins are each translated as a single-chain polypeptide of approximately 150 kDa that is subsequently cleaved by proteolytic scission within a disulfide loop by a naturally-occurring protease (FIG. 2). This cleavage occurs within the discrete di-chain loop region located between two cysteine residues that form a disulfide bridge and comprising an endogenous protease cleavage site. As used herein, the term "endogenous di-chain loop protease cleavage site" is synonymous with a "naturally occurring di-chain loop protease cleavage site" and refers to a naturally occurring protease cleavage site found within the di-chain loop region of a naturally occurring Clostridial toxin. This post-translational processing yields a di-chain molecule comprising an approximately 50 kDa light chain, comprising the enzymatic domain, and an approximately 100 kDa heavy chain, comprising the translocation and cell binding domains, the light chain and heavy chain being held together by the single disulfide bond and non-covalent interactions (FIG. 2). Recombinantly-produced Clostridial toxins generally substitute the naturally-occurring di-chain loop protease cleavage site with an exogenous protease cleavage site to facilitate production of a recombinant di-chain molecule (FIGS. 3-5). See e.g., Dolly, J. O. et al., Activatable Clostridial Toxins, U.S. Pat. No. 7,419,676 (Sep. 2, 2008), which is hereby incorporated by reference.

Although TEMs vary in their overall molecular weight because the size of the targeting domain, the activation process and its reliance on an exogenous cleavage site is essentially the same as that for recombinantly-produced Clostridial toxins. See e.g., Steward, et al., Activatable Clostridial Toxins, US 2009/0081730; Steward, et al., Modified Clostridial Toxins with Enhanced Translocation Capabilities and Altered Targeting Activity For Non-Clostridial Toxin Target Cells, U.S. patent application Ser. No. 11/776,075; Steward, et al., Modified Clostridial Toxins with Enhanced Translocation Capabilities and Altered Targeting Activity for Clostridial Toxin Target Cells, US 2008/0241881, each of which is hereby incorporated by reference. In general, the activation process that converts the single-chain polypeptide into its di-chain form using exogenous proteases can be used to process TEMs having a targeting domain organized in an amino presentation, central presentation, or carboxyl presentation arrangement. This is because for most targeting domains the amino-terminus of the moiety does not participate in receptor binding. As such, a wide range of protease cleavage sites can be used to produce an active di-chain form of a TEM. However, targeting domains requiring a free amino-terminus for receptor binding require a protease cleavage site whose scissile bond is located at the carboxyl terminus. The use of protease cleavage site is the design of a TEM are described in, e.g., Steward, et al., Activatable Clostridial toxins, US 2009/0069238; Ghanshani, et al., Modified Clostridial Toxins Comprising an Integrated Protease Cleavage Site-Binding Domain, US 2011/0189162; and Ghanshani, et al., Methods of Intracellular Conversion of Single-Chain Proteins into their Di-chain Form, International Patent Application Serial No. PCT/US2011/22272, each of which is incorporated by reference in its entirety.

Non-limiting examples of exogenous protease cleavage sites include, e.g., a plant papain cleavage site, an insect papain cleavage site, a crustacean papain cleavage site, an enterokinase protease cleavage site, a Tobacco Etch Virus protease cleavage site, a Tobacco Vein Mottling Virus protease cleavage site, a human rhinovirus 3C protease cleavage site, a human enterovirus 3C protease cleavage site, a subtilisin cleavage site, a hydroxylamine cleavage site, a SUMO/ULP-1 protease cleavage site, and a Caspase 3 cleavage site.

Figure 3A:
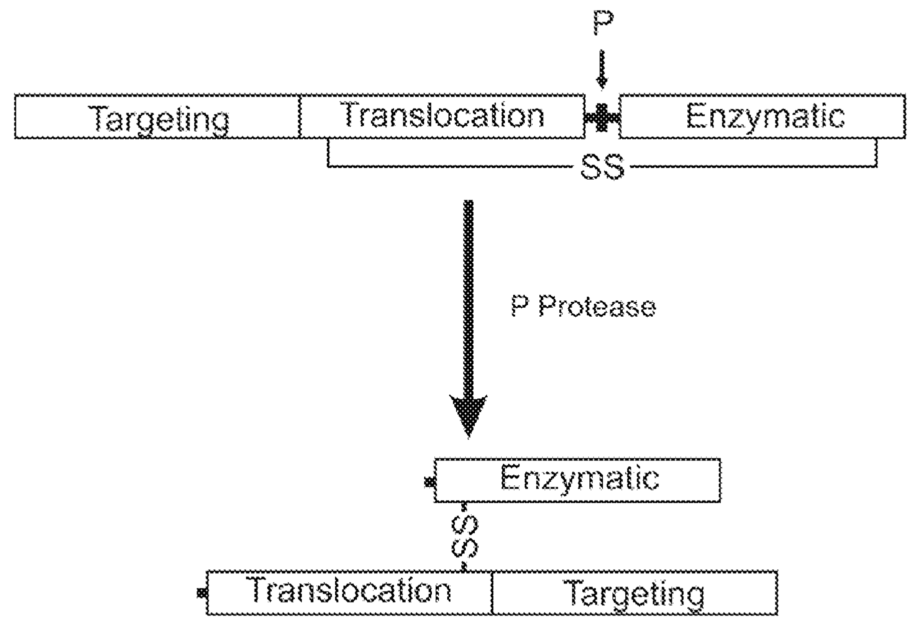
FIG. 3A depicts the single-chain polypeptide form of a TEM with an amino to carboxyl linear organization comprising a targeting domain, a translocation domain, a di-chain loop region comprising an exogenous protease cleavage site (P), and an enzymatic domain. Upon proteolytic cleavage with a P protease, the single-chain form of the TEM is converted to the di-chain form.

Thus, in an embodiment, a TEM can comprise an amino to carboxyl single polypeptide linear order comprising a targeting domain, a translocation domain, an exogenous protease cleavage site and an enzymatic domain (FIG. 3A). In an aspect of this embodiment, a TEM can comprise an amino to carboxyl single polypeptide linear order comprising a targeting domain, a Clostridial toxin translocation domain, an exogenous protease cleavage site and a Clostridial toxin enzymatic domain.

Figure 3B:
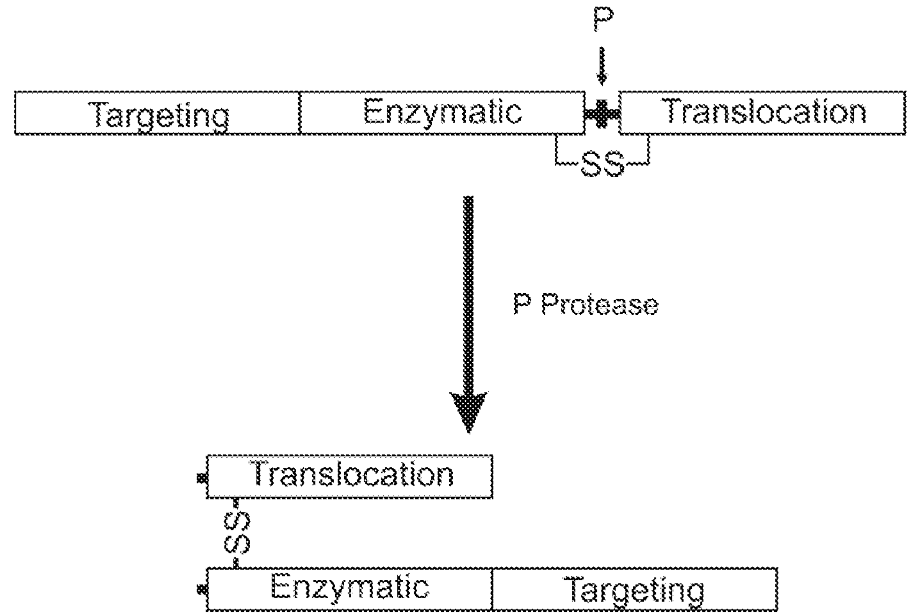
FIG. 3B depicts the single polypeptide form of a TEM with an amino to carboxyl linear organization comprising a targeting domain, an enzymatic domain, a di-chain loop region comprising an exogenous protease cleavage site (P), and a translocation domain. Upon proteolytic cleavage with a P protease, the single-chain form of the TEM is converted to the di-chain form.

In another embodiment, a TEM can comprise an amino to carboxyl single polypeptide linear order comprising a targeting domain, an enzymatic domain, an exogenous protease cleavage site, and a translocation domain (FIG. 3B). In an aspect of this embodiment, a TEM can comprise an amino to carboxyl single polypeptide linear order comprising a targeting domain, a Clostridial toxin enzymatic domain, an exogenous protease cleavage site, a Clostridial toxin translocation domain.

Figure 4A:
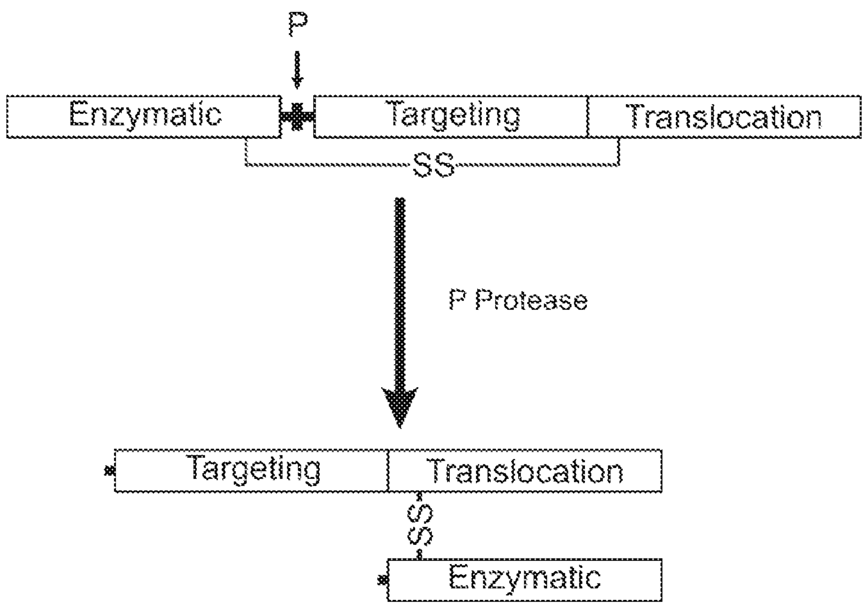
FIG. 4A depicts the single polypeptide form of a TEM with an amino to carboxyl linear organization comprising an enzymatic domain, a di-chain loop region comprising an exogenous protease cleavage site (P), a targeting domain, and a translocation domain. Upon proteolytic cleavage with a P protease, the single-chain form of the TEM is converted to the di-chain form.

In yet another embodiment, a TEM can comprise an amino to carboxyl single polypeptide linear order comprising an enzymatic domain, an exogenous protease cleavage site, a targeting domain, and a translocation domain (FIG. 4A). In an aspect of this embodiment, a TEM can comprise an amino to carboxyl single polypeptide linear order comprising a Clostridial toxin enzymatic domain, an exogenous protease cleavage site, a targeting domain, and a Clostridial toxin translocation domain.

Figure 4B:
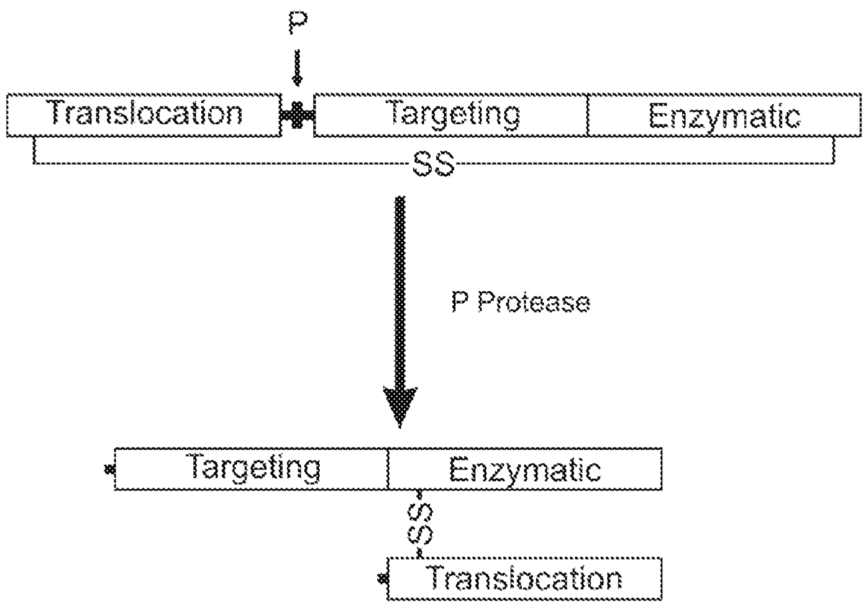
FIG. 4B depicts the single polypeptide form of a TEM with an amino to carboxyl linear organization comprising a translocation domain, a di-chain loop region comprising an exogenous protease cleavage site (P), a targeting domain, and an enzymatic domain. Upon proteolytic cleavage with a P protease, the single-chain form of the TEM is converted to the di-chain form.

In yet another embodiment, a TEM can comprise an amino to carboxyl single polypeptide linear order comprising a translocation domain, an exogenous protease cleavage site, a targeting domain, and an enzymatic domain (FIG. 4B). In an aspect of this embodiment, a TEM can comprise an amino to carboxyl single polypeptide linear order comprising a Clostridial toxin translocation domain, a targeting domain, an exogenous protease cleavage site and a Clostridial toxin enzymatic domain.

Figure 4C:
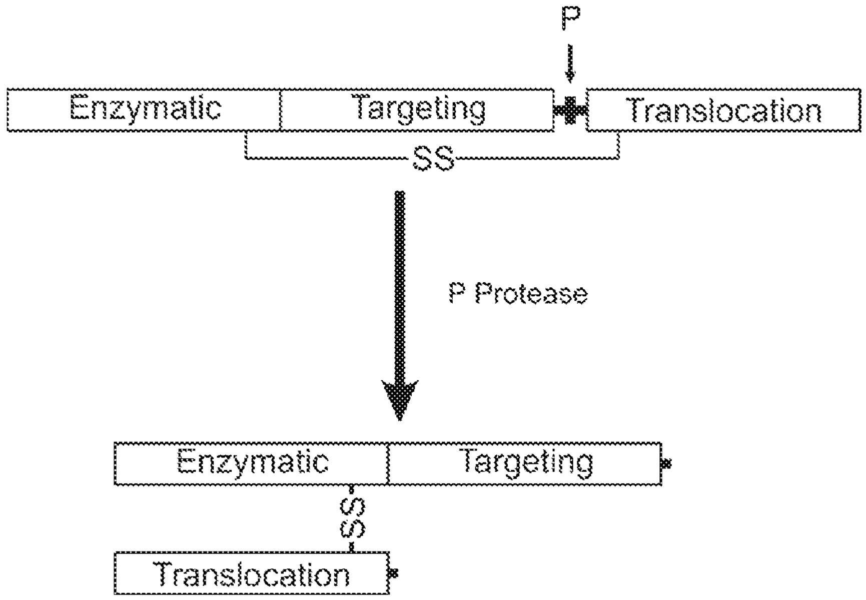
FIG. 4C depicts the single polypeptide form of a TEM with an amino to carboxyl linear organization comprising an enzymatic domain, a targeting domain, a di-chain loop region comprising an exogenous protease cleavage site (P), and a translocation domain. Upon proteolytic cleavage with a P protease, the single-chain form of the TEM is converted to the di-chain form.

In another embodiment, a TEM can comprise an amino to carboxyl single polypeptide linear order comprising an enzymatic domain, a targeting domain, an exogenous protease cleavage site, and a translocation domain (FIG. 4C). In an aspect of this embodiment, a TEM can comprise an amino to carboxyl single polypeptide linear order comprising a Clostridial toxin enzymatic domain, a targeting domain, an exogenous protease cleavage site, a Clostridial toxin translocation domain.

Figure 4D:
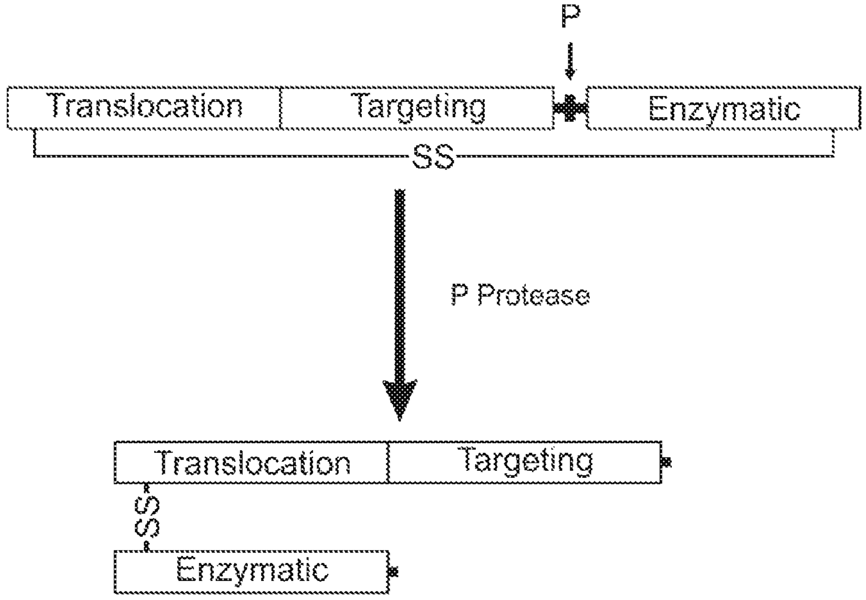
FIG. 4D depicts the single polypeptide form of a TEM with an amino to carboxyl linear organization comprising a translocation domain, a targeting domain, a di-chain loop region comprising an exogenous protease cleavage site (P), and an enzymatic domain. Upon proteolytic cleavage with a P protease, the single-chain form of the TEM is converted to the di-chain form.

In yet another embodiment, a TEM can comprise an amino to carboxyl single polypeptide linear order comprising a translocation domain, a targeting domain, an exogenous protease cleavage site and an enzymatic domain (FIG. 4D). In an aspect of this embodiment, a TEM can comprise an amino to carboxyl single polypeptide linear order comprising a Clostridial toxin translocation domain, a targeting domain, an exogenous protease cleavage site and a Clostridial toxin enzymatic domain.

Figure 5A:
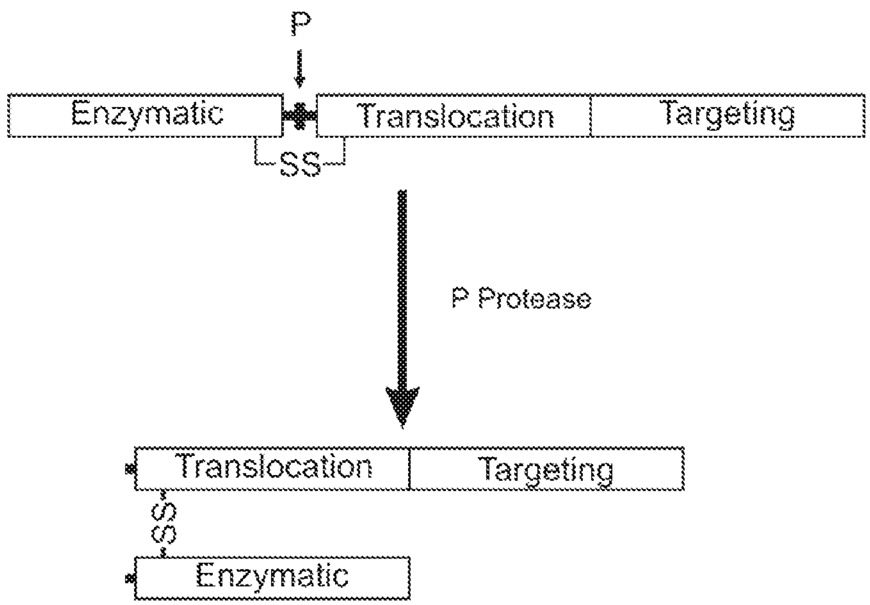
FIG. 5A depicts the single polypeptide form of a TEM with an amino to carboxyl linear organization comprising an enzymatic domain, a di-chain loop region comprising an exogenous protease cleavage site (P), a translocation domain, and a targeting domain. Upon proteolytic cleavage with a P protease, the single-chain form of the TEM is converted to the di-chain form.

In still another embodiment, a TEM can comprise an amino to carboxyl single polypeptide linear order comprising an enzymatic domain, an exogenous protease cleavage site, a translocation domain, and a targeting domain (FIG. 5A). In an aspect of this embodiment, a TEM can comprise an amino to carboxyl single polypeptide linear order comprising a Clostridial toxin enzymatic domain, an exogenous protease cleavage site, a Clostridial toxin translocation domain, and a targeting domain.

Figure 5B:
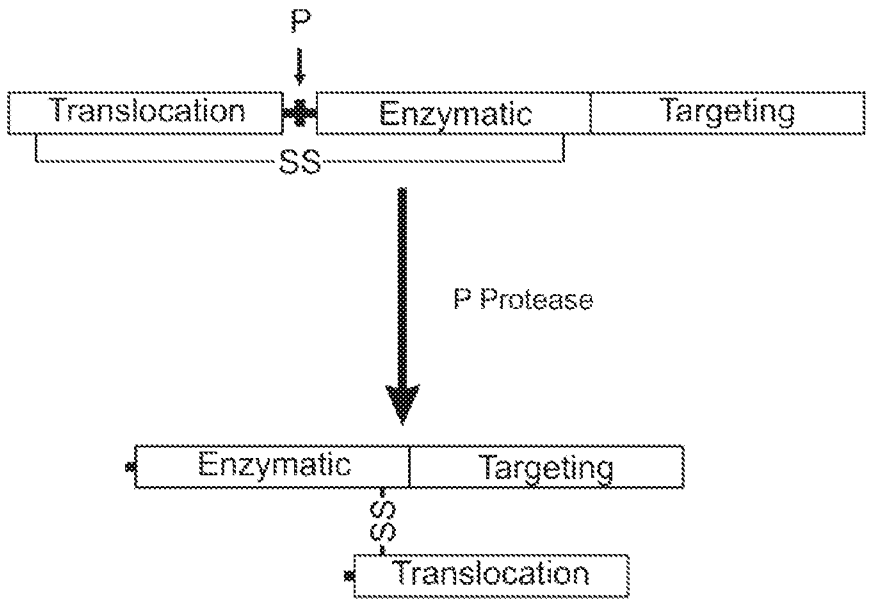
FIG. 5B depicts the single polypeptide form of a TEM with an amino to carboxyl linear organization comprising a translocation domain, a di-chain loop region comprising an exogenous protease cleavage site (P), an enzymatic domain, and a targeting domain. Upon proteolytic cleavage with a P protease, the single-chain form of the TEM is converted to the di-chain form.

In still another embodiment, a TEM can comprise an amino to carboxyl single polypeptide linear order comprising a translocation domain, an exogenous protease cleavage site, an enzymatic domain and a targeting domain, (FIG. 5B). In an aspect of this embodiment, a TEM can comprise an amino to carboxyl single polypeptide linear order comprising a Clostridial toxin translocation domain, a targeting domain, an exogenous protease cleavage site and a Clostridial toxin enzymatic domain.

Non-limiting examples of TEMs disclosed herein, including TEMs comprising a Clostridial toxin enzymatic domain, a Clostridial toxin translocation domain and a targeting domain, the use of an exogenous protease cleavage site, and the design of amino presentation, central presentation and carboxyl presentation TEMs are described in, e.g., U.S. Pat. No. 7,959,933, Activatable Recombinant Neurotoxins, U.S. Pat. No. 7,897,157, Activatable Clostridial Toxins; U.S. Pat. No. 7,833,535, Clostridial Toxin Derivatives and Methods for Treating Pain; U.S. Pat. No. 7,811,584, Multivalent Clostridial Toxins; U.S. Pat. No. 7,780,968, Clostridial Toxin Derivatives and Methods for Treating Pain; U.S. Pat. No. 7,749,514, Activatable Clostridial Toxins, U.S. Pat. No. 7,740,868, Activatable Clostridial Toxins; U.S. Pat. No. 7,736,659, Clostridial Toxin Derivatives and Methods for Treating Pain; U.S. Pat. No. 7,709,228, Activatable Recombinant Neurotoxins; U.S. Pat. No. 7,704,512, Clostridial Toxin Derivatives and Methods for Treating Pain; U.S. Pat. No. 7,659,092, Fusion Proteins; U.S. Pat. No. 7,658,933, Non-Cytotoxic Protein Conjugates; U.S. Pat. No. 7,622,127, Clostridial Toxin Derivatives and Methods for Treating Pain; U.S. Pat. No. 7,514,088, Multivalent Clostridial Toxin Derivatives and Methods of Their Use; U.S. Pat. No. 7,425,338, Clostridial Toxin Derivatives and Methods for Treating Pain; U.S. Pat. No. 7,422,877, Activatable Recombinant Neurotoxins; U.S. Pat. No. 7,419,676, Activatable Recombinant Neurotoxins; U.S. Pat. No. 7,413,742, Clostridial Toxin Derivatives and Methods for Treating Pain; U.S. Pat. No. 7,262,291, Clostridial Toxin Derivatives and Methods for Treating Pain; U.S. Pat. No. 7,244,437, Clostridial Toxin Derivatives and Methods for Treating Pain; U.S. Pat. No. 7,244,436, Clostridial Toxin Derivatives and Methods for Treating Pain; U.S. Pat. No. 7,138,127, Clostridial Toxin Derivatives and Methods for Treating Pain; U.S. Pat. No. 7,132,259, Activatable Recombinant Neurotoxins; U.S. Pat. No. 7,056,729, Botulinum Neurotoxin-Substance P Conjugate or Fusion Protein for Treating Pain; U.S. Pat. No. 6,641,820, Clostridial Toxin Derivatives and Methods to Treat Pain; U.S. Pat. No. 6,500,436, Clostridial Toxin Derivatives and Methods for Treating Pain; US 2011/0091437, Fusion Proteins; US 2011/0070621, Multivalent Clostridial Toxins; US 2011/0027256, Fusion Proteins; US 2010/0247509, Fusion Proteins; US 2010/0041098, Modified Clostridial Toxins with Altered Targeting Capabilities for Clostridial Toxin Target Cells; US 2010/0034802, Treatment of Pain; US 2009/0162341, Non-Cytotoxic Protein Conjugates; US 2009/0087458, Activatable Recombinant Neurotoxins; US 2009/0081730, Activatable Recombinant Neurotoxins; US 2009/0069238, Activatable Clostridial Toxins; US 2009/0042270, Activatable Recombinant Neurotoxins; US 2009/0030182, Activatable Recombinant Neurotoxins; US 2009/0018081, Activatable Clostridial Toxins; US 2009/0005313, Activatable Clostridial Toxins; US 2009/0004224, Activatable Clostridial Toxins; US 2008/0317783, Clostridial Toxin Derivatives and Methods for Treating Pain; US 2008/0241881, Modified Clostridial Toxins with Enhanced Translocation Capabilities and Altered Targeting Activity for Clostridial Toxin Target Cells; WO 2006/099590, Modified Clostridial Toxins with Altered Targeting Capabilities for Clostridial Toxin Target Cells; WO 2006/101809, Modified Clostridial Toxins with Enhanced Targeting Capabilities for Endogenous Clostridial Toxin Receptor Systems; WO 2007/106115, Modified Clostridial Toxins with Altered Targeting Capabilities for Clostridial Toxin Target Cells; WO 2008/008803, Modified Clostridial Toxins with Enhanced Translocation Capabilities and Altered Targeting Activity for Clostridial Toxin Target Cells; WO 2008/008805, Modified Clostridial Toxins with Enhanced Translocation Capabilities and Altered Targeting Activity For Non-Clostridial Toxin Target Cells; WO 2008/105901, Modified Clostridial Toxins with Enhanced Translocation Capability and Enhanced Targeting Activity; WO 2011/020052, Methods of Treating Cancer Using Opioid Retargeted Endopeptidases; WO 2011/020056, Methods of Treating Cancer Using Galanin Retargeted Endopeptidases; WO 2011/020114, Methods of Treating Cancer Using Tachykinin Retargeted Endopeptidases; WO 2011/020115, Methods of Treating Cancer Using Growth Factor Retargeted Endopeptidases; WO 2011/020117, Methods of Treating Cancer Using Neurotrophin Retargeted Endopeptidases; WO 2011/020119, Methods of Treating Cancer Using Glucagon-Like Hormone Retargeted Endopeptidases; each incorporated entirely by reference.

Aspects of the present specification disclose, in part, a composition. In one aspect of this embodiment, a composition comprises a TEM as disclosed herein. In another aspect of this embodiment, a composition comprises a Clostridial toxin and a TEM as disclosed herein. Any of the compositions disclosed herein can be useful in a method of treating disclosed herein, with the proviso that the composition prevents or reduces a symptom associated with condition being treated. A Clostridial toxin and a TEM as disclosed herein may be provided as separate compositions or as part of a single composition. It is also understood that the two or more different Clostridial toxins and/or TEMs can be provided as separate compositions or as part of a single composition.

A composition disclosed herein is generally administered as a pharmaceutical acceptable composition. As used herein, the term "pharmaceutically acceptable" means any molecular entity or composition that does not produce an adverse, allergic or other untoward or unwanted reaction when administered to an individual. As used herein, the term "pharmaceutically acceptable composition" is synonymous with "pharmaceutical composition" and means a therapeutically effective concentration of an active ingredient, such as, e.g., any of the Clostridial toxins and/or TEMs disclosed herein. A pharmaceutical composition disclosed herein is useful for medical and veterinary applications. A pharmaceutical composition may be administered to an individual alone, or in combination with other supplementary active ingredients, agents, drugs or hormones. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilizate, tablet, pill, pellet, capsule, powder, syrup, elixir or any other dosage form suitable for administration.

A pharmaceutical composition disclosed herein may optionally include a pharmaceutically acceptable carrier that facilitates processing of an active ingredient into pharmaceutically acceptable compositions. As used herein, the term "pharmacologically acceptable carrier" is synonymous with "pharmacological carrier" and means any carrier that has substantially no long term or permanent detrimental effect when administered and encompasses terms such as "pharmacologically acceptable vehicle, stabilizer, diluent, additive, auxiliary or excipient." Such a carrier generally is mixed with an active ingredient, or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in PHARMACEUTICAL DOSAGE FORMS AND DRUG DELIVERY SYSTEMS (Howard C. Ansel et al., eds., Lippincott Williams & Wilkins Publishers, 7th ed. 1999); REMINGTON: THE SCIENCE AND PRACTICE OF PHARMACY (Alfonso R. Gennaro ed., Lippincott, Williams & Wilkins, 20th ed. 2000); GOODMAN & GILMAN'S THE PHARMACOLOGICAL BASIS OF THERAPEUTICS (Joel G. Hardman et al., eds., McGraw-Hill Professional, 10th ed. 2001); and HANDBOOK OF PHARMACEUTICAL EXCIPIENTS (Raymond C. Rowe et al., APhA Publications, 4th edition 2003). These protocols are routine procedures and any modifications are well within the scope of one skilled in the art and from the teaching herein.

A pharmaceutical composition disclosed herein can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed herein, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition and chelants, such as, e.g., DTPA or DTPA-bisamide, calcium DTPA, and CaNa-DTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition. Exemplary pharmaceutical composition comprising a TEM are described in Hunt, et al., Animal Protein-Free Pharmaceutical Compositions, U.S. Ser. No. 12/331,816; and Dasari, et al., Clostridial Toxin Pharmaceutical Compositions, WO/2010/090677, each incorporated entirely by reference.

In an embodiment, a composition is a pharmaceutical composition comprising a TEM. In aspects of this embodiment, a pharmaceutical composition comprising a TEM further comprises a pharmacological carrier, a pharmaceutical component, or both a pharmacological carrier and a pharmaceutical component. In other aspects of this embodiment, a pharmaceutical composition comprising a TEM further comprises at least one pharmacological carrier, at least one pharmaceutical component, or at least one pharmacological carrier and at least one pharmaceutical component.

In another embodiment, a composition is a pharmaceutical composition comprising a Clostridial toxin. In aspects of this embodiment, a pharmaceutical composition comprising a Clostridial toxin further comprises a pharmacological carrier, a pharmaceutical component, or both a pharmacological carrier and a pharmaceutical component. In other aspects of this embodiment, a pharmaceutical composition comprising a Clostridial toxin further comprises at least one pharmacological carrier, at least one pharmaceutical component, or at least one pharmacological carrier and at least one pharmaceutical component.

In yet another embodiment, a composition is a pharmaceutical composition comprising a Clostridial toxin and a TEM. In aspects of this embodiment, a pharmaceutical composition comprising a Clostridial toxin and a TEM further comprises a pharmacological carrier, a pharmaceutical component, or both a pharmacological carrier and a pharmaceutical component. In other aspects of this embodiment, a pharmaceutical composition comprising a Clostridial toxin and a TEM further comprises at least one pharmacological carrier, at least one pharmaceutical component, or at least one pharmacological carrier and at least one pharmaceutical component.

A post-traumatic stress disorder (PTSD) refers to a disorder where an individual has one or more symptoms due to an over-reactive adrenaline response to a triggering traumatic event, which creates neurological patterns in the brain and biochemical changes in the brain and body that persist long after the triggering event is over. As a result, an individual affected with a PTSD is hyper-responsive to future fearful or stressful events. Some biochemical changes seen in PTSD sufferers include a low level of secretion of cortisol and a high level of secretion of catecholamines and corticotropin-releasing factor in the urine.

Symptoms of a PTSD can include, without limitation: amnesia regarding parts or all of the event; anger; avoidance of people, places or things that may serve as reminders of the event; flashbacks, dreams or other memories that cause the sufferer to re-experience the traumatic event; hypervigilance; insomnia; lack of concentration; emotional numbing of or complete inability to feel certain feelings; an intensely negative response, either psychological or physiological or both, to reminders of the event; reduction in ability to participate in significant life activities; and, a significant impairment of major areas of life activity, such as social relations, work, etc. Additionally, alcohol and drug abuse can commonly co-occur with a PTSD, and other psychological disorders (such as an anxiety disorder) can be exacerbated or worsened). In some cases a PTSD can become chronic.

A composition or compound is administered to an individual. An individual comprises all mammals, preferably a human being. Typically, any individual who is a candidate for a conventional psychological trauma disorder treatment is a candidate for a psychological trauma disorder treatment disclosed herein. Pre-operative evaluation typically includes routine history and physical examination in addition to thorough informed consent disclosing all relevant risks and benefits of the procedure.

With reference to a therapy comprising a TEM, the amount of a TEM disclosed herein used with the methods of treatment disclosed herein will typically be an effective amount. As used herein, the term “effective amount” is synonymous with “therapeutically effective amount”, “effective dose”, or “therapeutically effective dose” and when used in reference to treating a psychological trauma disorder means the minimum dose of a TEM alone necessary to achieve the desired therapeutic effect and includes a dose sufficient to reduce a symptom associated with a psychological trauma disorder. An effective amount refers to the total amount of a TEM administered to an individual in one setting. As such, an effective amount of a TEM does not refer to the amount administered per site. The effectiveness of a TEM disclosed herein in treating a psychological trauma disorder can be determined by observing an improvement in an individual based upon one or more clinical symptoms, and/or physiological indicators associated with the condition. An improvement in a psychological trauma disorder also can be indicated by a reduced need for a concurrent therapy.

With reference to a standard dose combination therapy comprising a Clostridial toxin and a TEM, an effective amount of a Clostridial toxin is one where in combination with a TEM the amount of a Clostridial toxin achieves the desired therapeutic effect. For example, typically about 29-195 U of BOTOX® (Allergan, Inc., Irvine, Calif.), a BoNT/A, is administered in order to treat a psychological trauma disorder. As one example, a patient may be treated according to the PREEMPT paradigm with 155 U BoNT/A. In another case, a female patient may be treated using a glabellar administration paradigm with a total of about 30 U BoNT/A, a male patient treated using a glabellar administration paradigm with a total of about 40 U BoNT/A.

Generally, the PREEMPT paradigm refers to administration to: the frontalis at divided among four sites of administration; to the corrugator divided among two sites of administration; to the procerus at one site of administration; to the occipitalis at six sites to eight sites of administration; to the temporalis at eight sites to ten sites of administration; to the trapezius at six sites to ten sites of administration and to the cervical paraspinal muscles at four sites of administration. In one embodiment, a total of 155 units of BoNT/A are administered at 31 sites.

With reference to a low dose combination therapy comprising a Clostridial toxin and a TEM, an effective amount of a Clostridial toxin is one where in combination with a TEM the amount of a Clostridial toxin achieves the desired therapeutic effect, but such an amount administered on its own would be ineffective. For example, typically about 29-195 U of BOTOX® (Allergan, Inc., Irvine, Calif.), a BoNT/A, is administered in order to treat a psychological trauma disorder. However, in a low dose combination therapy, a suboptimal effective amount of BoNT/A would be administered to treat a psychological trauma disorder when such toxin is used in a combined therapy with a TEM. For example, less that 50 U, less than 25 U, less than 15 U, less than 10 U, less than 7.5 U, less than 5 U, less than 2.5 U, or less than 1 U of BoNT/A would be administered to treat a psychological trauma disorder when used in a low dose combination therapy with a TEM as disclosed herein.

The appropriate effective amount of a Clostridial toxin and/or a TEM to be administered to an individual for a particular psychological trauma disorder can be determined by a person of ordinary skill in the art by taking into account factors, including, without limitation, the type of psychological trauma disorder, the location of the psychological trauma disorder, the cause of the psychological trauma disorder, the severity of the psychological trauma disorder, the degree of relief desired, the duration of relief desired, the particular Clostridial toxin and/or a TEM used, the rate of excretion of the Clostridial toxin and/or a TEM used, the pharmacodynamics of the Clostridial toxin and/or a TEM used, the nature of the other compounds to be included in the composition, the particular route of administration, the particular characteristics, history and risk factors of the individual, such as, e.g., age, weight, general health and the like, or any combination thereof. Additionally, where repeated administration of a composition comprising disclosed herein is used, an effective amount of a Clostridial toxin and/or a TEM will further depend upon factors, including, without limitation, the frequency of administration, the half-life of the composition comprising a Clostridial toxin and/or a TEM, or any combination thereof. In is known by a person of ordinary skill in the art that an effective amount of a composition comprising a Clostridial toxin and/or a TEM can be extrapolated from in vitro assays and in vivo administration studies using animal models prior to administration to humans.

Wide variations in the necessary effective amount are to be expected in view of the differing efficiencies of the various routes of administration. For instance, oral administration generally would be expected to require higher dosage levels than administration by intravenous or intravitreal injection. Similarly, systemic administration of a TEM would be expected to require higher dosage levels than a local administration. Variations in these dosage levels can be adjusted using standard empirical routines of optimization, which are well-known to a person of ordinary skill in the art. The precise therapeutically effective dosage levels and patterns are preferably determined by the attending physician in consideration of the above-identified factors. One skilled in the art will recognize that the condition of the individual can be monitored throughout the course of therapy and that the effective amount of a TEM disclosed herein that is administered can be adjusted accordingly.

In aspects of this embodiment, a therapeutically effective amount of a composition comprising a TEM reduces a symptom associated with a psychological trauma disorder by, e.g., at least 10%, at least 20%, at least 30%, at least 40%, at least 50%, at least 60%, at least 70%, at least 80%, at least 90% or at least 100%. In other aspects of this embodiment, a therapeutically effective amount of a composition comprising a TEM reduces a symptom associated with a psychological trauma disorder by, e.g., at most 10%, at most 20%, at most 30%, at most 40%, at most 50%, at most 60%, at most 70%, at most 80%, at most 90% or at most 100%. In yet other aspects of this embodiment, a therapeutically effective amount of a composition comprising a TEM reduces a symptom associated with a psychological trauma disorder by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%. In still other aspects of this embodiment, a therapeutically effective amount of the TEM is the dosage sufficient to inhibit neuronal activity for, e.g., at least one week, at least one month, at least two months, at least three months, at least four months, at least five months, at least six months, at least seven months, at least eight months, at least nine months, at least ten months, at least eleven months, or at least twelve months.

In other aspects of this embodiment, a therapeutically effective amount of a TEM generally is in the range of about 1 fg to about 3.0 mg. In aspects of this embodiment, an effective amount of a TEM can be, e.g., about 100 fg to about 3.0 mg, about 100 pg to about 3.0 mg, about 100 ng to about 3.0 mg, or about 100 μg to about 3.0 mg. In other aspects of this embodiment, an effective amount of a TEM can be, e.g., about 100 fg to about 750 μg, about 100 pg to about 750 μg, about 100 ng to about 750 μg, or about 1 μg to about 750 μg. In yet other aspects of this embodiment, a therapeutically effective amount of a TEM can be, e.g., at least 1 fg, at least 250 fg, at least 500 fg, at least 750 fg, at least 1 pg, at least 250 pg, at least 500 pg, at least 750 pg, at least 1 ng, at least 250 ng, at least 500 ng, at least 750 ng, at least 1 μg, at least 250 μg, at least 500 μg, at least 750 μg, or at least 1 mg. In still other aspects of this embodiment, a therapeutically effective amount of a composition comprising a TEM can be, e.g., at most 1 fg, at most 250 fg, at most 500 fg, at most 750 fg, at most 1 μg, at most 250 μg, at most 500 pg, at most 750 pg, at most 1 ng, at most 250 ng, at most 500 ng, at most 750 ng, at most 1 μg, at least 250 μg, at most 500 μg, at most 750 μg, or at most 1 mg.

In yet other aspects of this embodiment, a therapeutically effective amount of a TEM generally is in the range of about 0.00001 mg/kg to about 3.0 mg/kg. In aspects of this embodiment, an effective amount of a TEM can be, e.g., about 0.0001 mg/kg to about 0.001 mg/kg, about 0.03 mg/kg to about 3.0 mg/kg, about 0.1 mg/kg to about 3.0 mg/kg, or about 0.3 mg/kg to about 3.0 mg/kg. In yet other aspects of this embodiment, a therapeutically effective amount of a TEM can be, e.g., at least 0.00001 mg/kg, at least 0.0001 mg/kg, at least 0.001 mg/kg, at least 0.01 mg/kg, at least 0.1 mg/kg, or at least 1 mg/kg. In yet other aspects of this embodiment, a therapeutically effective amount of a TEM can be, e.g., at most 0.00001 mg/kg, at most 0.0001 mg/kg, at most 0.001 mg/kg, at most 0.01 mg/kg, at most 0.1 mg/kg, or at most 1 mg/kg.

In aspects of this embodiment, a therapeutically effective amount of a composition comprising a Clostridial toxin reduces a symptom associated with a psychological trauma disorder by, e.g., at least 10%, at least 20%, at least 30%, at least 40%, at least 50%, at least 60%, at least 70%, at least 80%, at least 90% or at least 100%. In other aspects of this embodiment, a therapeutically effective amount of a composition comprising a Clostridial toxin reduces a symptom associated with a psychological trauma disorder by, e.g., at most 10%, at most 20%, at most 30%, at most 40%, at most 50%, at most 60%, at most 70%, at most 80%, at most 90% or at most 100%. In yet other aspects of this embodiment, a therapeutically effective amount of a composition comprising a Clostridial toxin reduces a symptom associated with a psychological trauma disorder by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%. In still other aspects of this embodiment, a therapeutically effective amount of a Clostridial toxin is the dosage sufficient to inhibit neuronal activity for, e.g., at least one week, at least one month, at least two months, at least three months, at least four months, at least five months, at least six months, at least seven months, at least eight months, at least nine months, at least ten months, at least eleven months, or at least twelve months.

In other aspects of this embodiment, a therapeutically effective amount of a Clostridial toxin generally is in the range of about 1 fg to about 30.0 μg. In other aspects of this embodiment, a therapeutically effective amount of a Clostridial toxin can be, e.g., at least 1.0 pg, at least 10 pg, at least 100 pg, at least 1.0 ng, at least 10 ng, at least 100 ng, at least 1.0 μg, at least 10 μg, at least 100 μg, or at least 1.0 mg. In still other aspects of this embodiment, a therapeutically effective amount of a Clostridial toxin can be, e.g., at most 1.0 pg, at most 10 pg, at most 100 pg, at most 1.0 ng, at most 10 ng, at most 100 ng, at most 1.0 μg, at most 10 μg, at most 100 μg, or at most 1.0 mg. In still other aspects of this embodiment, a therapeutically effective amount of a Clostridial toxin can be, e.g., about 1.0 pg to about 10 μg, about 10 pg to about 10 μg, about 100 μg to about 10 pg, about 1.0 ng to about 10 μg, about 10 ng to about 10 μg, or about 100 ng to about 10 μg. In still other aspects of this embodiment, a therapeutically effective amount of a Clostridial toxin can be from, e.g., about 1.0 pg to about 1.0 μg, about 10 pg to about 1.0 μg, about 100 pg to about 1.0 μg, about 1.0 ng to about 1.0 μg, about 10 ng to about 1.0 μg, or about 100 ng to about 1.0 μg. In other aspects of this embodiment, a therapeutically effective amount of a Clostridial toxin can be from, e.g., about 1.0 pg to about 100 ng, about 10 pg to about 100 ng, about 100 pg to about 100 ng, about 1.0 ng to about 100 ng, or about 10 ng to about 100 ng.

In yet other aspects of this embodiment, a therapeutically effective amount of a Clostridial toxin generally is in the range of about 0.1 U to about 2500 U. In other aspects of this embodiment, a therapeutically effective amount of a Clostridial toxin can be, e.g., at least 1.0 U, at least 10 U, at least 100 U, at least 250 U, at least 500 U, at least 750 U, at least 1,000 U, at least 1,500 U, at least 2,000 U, or at least 2,500 U. In still other aspects of this embodiment, a therapeutically effective amount of a Clostridial toxin can be, e.g., at most 1.0 U, at most 10 U, at most 100 U, at most 250 U, at most 500 U, at most 750 U, at most 1,000 U, at most 1,500 U, at most 2,000 U, or at most 2,500 U. In still other aspects of this embodiment, a therapeutically effective amount of a Clostridial toxin can be, e.g., about 1 U to about 2,000 U, about 10 U to about 2,000 U, about 50 U to about 2,000 U, about 100 U to about 2,000 U, about 500 U to about 2,000 U, about 1,000 U to about 2,000 U, about 1 U to about 1,000 U, about 10 U to about 1,000 U, about 50 U to about 1,000 U, about 100 U to about 1,000 U, about 500 U to about 1,000 U, about 1 U to about 500 U, about 10 U to about 500 U, about 50 U to about 500 U, about 100 U to about 500 U, about 1 U to about 100 U, about 10 U to about 100 U, about 50 U to about 100 U, about 0.1 U to about 1 U, about 0.1 U to about 5 U, about 0.1 U to about 10 U, about 0.1 U to about 15 U, about 0.1 U to about 20 U, about 0.1 U to about 25 U.

In still other aspects of this embodiment, a therapeutically effective amount of a Clostridial toxin generally is in the range of about 0.0001 U/kg to about 3,000 U/kg. In aspects of this embodiment, a therapeutically effective amount of a Clostridial toxin can be, e.g., at least 0.001 U/kg, at least 0.01 U/kg, at least 0.1 U/kg, at least 1.0 U/kg, at least 10 U/kg, at least 100 U/kg, or at least 1000 U/kg. In other aspects of this embodiment, a therapeutically effective amount of a Clostridial toxin can be, e.g., at most 0.001 U/kg, at most 0.01 U/kg, at most 0.1 U/kg, at most 1.0 U/kg, at most 10 U/kg, at most 100 U/kg, or at most 1000 U/kg. In yet other aspects of this embodiment, a therapeutically effective amount of a Clostridial toxin can be between, e.g., about 0.001 U/kg to about 1 U/kg, about 0.01 U/kg to about 1 U/kg, about 0.1 U/kg to about 1 U/kg, about 0.001 U/kg to about 10 U/kg, about 0.01 U/kg to about 10 U/kg, about 0.1 U/kg to about 10 U/kg about 1 U/kg to about 10 U/kg, about 0.001 U/kg to about 100 U/kg, about 0.01 U/kg to about 100 U/kg, about 0.1 U/kg to about 100 U/kg, about 1 U/kg to about 100 U/kg, or about 10 U/kg to about 100 U/kg. As used herein, the term "unit" or "U" is refers to the $LD_{50}$ dose, which is defined as the amount of a Clostridial toxin disclosed herein that killed 50% of the mice injected with the Clostridial toxin.

In aspects of this embodiment, a therapeutically effective amount of a standard or low combination therapy comprising a Clostridial toxin and a TEM reduces a symptom associated with a psychological trauma disorder by, e.g., at least 10%, at least 20%, at least 30%, at least 40%, at least 50%, at least 60%, at least 70%, at least 80%, at least 90% or at least 100%. In other aspects of this embodiment, a therapeutically effective amount of a standard or low combination therapy comprising a Clostridial toxin and a TEM reduces a symptom associated with a psychological trauma disorder by, e.g., at most 10%, at most 20%, at most 30%, at most 40%, at most 50%, at most 60%, at most 70%, at most 80%, at most 90% or at most 100%. In yet other aspects of this embodiment, a therapeutically effective amount of a standard or low combination therapy comprising a Clostridial toxin and a TEM reduces a symptom associated with a psychological trauma disorder by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%. In still other aspects of this embodiment, a therapeutically effective amount of a standard or low combination therapy comprising a Clostridial toxin and a TEM is the dosage sufficient to inhibit neuronal activity for, e.g., at least one week, at least one month, at least two months, at least three months, at least four months, at least five months, at least six months, at least seven months, at least eight months, at least nine months, at least ten months, at least eleven months, or at least twelve months.

In other aspects of this embodiment, a therapeutically effective amount of a standard or low combination therapy comprising a Botulinum toxin and a TEM generally is in a botulinum toxin: TEM molar ratio of about 1:1 to about 1:10,000. In other aspects of this embodiment, a therapeutically effective amount of a standard or low combination therapy comprising a botulinum toxin and a TEM can be in a botulinum toxin: TEM molar ratio of, e.g., about 1:1, about 1:2, about 1:5, about 1:10, about 1:25, about 1:50, about 1:75, about 1:100, about 1:200, about 1:300, about 1:400, about 1:500, about 1:600, about 1:700, about 1:800, about 1:900, about 1:1000, about 1:2000, about 1:3000, about 1:4000, about 1:5000, about 1:6000, about 1:7000, about 1:8000, about 1:9000, or about 1:10,000. In yet other aspects of this embodiment, a therapeutically effective amount of standard or low combination therapy comprising a botulinum toxin and a TEM can be in a botulinum toxin: TEM molar ratio of, e.g., at least 1:1, at least 1:2, at least 1:5, at least 1:10, at least 1:25, at least 1:50, at least 1:75, at least 1:100, at least 1:200, at least 1:300, at least 1:400, at least 1:500, at least 1:600, at least 1:700, at least 1:800, at least 1:900, at least 1:1000, at least 1:2000, at least 1:3000, at least 1:4000, at least 1:5000, at least 1:6000, at least 1:7000, at least 1:8000, at least 1:9000, or at least 1:10,000. In still other aspects of this embodiment, a therapeutically effective amount of a standard or low combination therapy comprising a botulinum toxin and a TEM can be in a botulinum toxin: TEM molar ratio of between, e.g., about 1:1 to about 1:10,000, about 1:10 to about 1:10,000, about 1:100 to about 1:10,000, about 1:500 to about 1:10,000, about 1:1000 to about 1:10,000, about 1:5000 to about 1:10,000, about 1:1 to about 1:1000, about 1:10 to about 1:1000, about 1:100 to about 1:1000, about 1:250 to about 1:1000, about 1:500 to about 1:1000, about 1:750 to about 1:1000, about 1:1 to about 1:500, about 1:10 to about 1:500, about 1:50 to about 1:500, about 1:100 to about 1:500, about 1:250 to about 1:500, about 1:1 to about 1:100, about 1:10 to about 1:100, about 1:25 to about 1:100, about 1:50 to about 1:100, or about 1:75 to about 1:100.

In yet other aspects of this embodiment, a therapeutically effective amount of a standard combination therapy comprising a botulinum toxin and a TEM generally is in a range of about 0.50 U to about 250 U of botulinum toxin and about 0.1 μg to about 2,000.0 μg of a TEM. In aspects of this embodiment, a therapeutically effective amount of a combined therapy comprising a botulinum toxin and a TEM can be, e.g., about 0.1 U to about 10 U of a botulinum toxin and about 10 μg to about 1,000 μg of a TEM, about 0.1 U to about 10 U of a botulinum toxin and about 10 μg to about 500 μg of a TEM, about 0.1 U to about 10 U of a botulinum toxin and about 10 μg to about 100 μg of a TEM, about 0.5 U to about 10 U of a botulinum toxin and about 10 μg to about 1,000 μg of a TEM, about 0.5 U to about 10 U of a botulinum toxin and about 10 μg to about 500 μg of a TEM, about 0.5 U to about 10 U of a botulinum toxin and about 10 μg to about 100 μg of a TEM, about 1 U to about 10 U of a botulinum toxin and about 100 μg to about 1,000 μg of a TEM, about 1 U to about 10 U of a botulinum toxin and about 100 μg to about 500 μg of a TEM, or about 1 U to about 10 U of a botulinum toxin and about 100 μg to about 100 μg of a TEM.

In yet other aspects of this embodiment, a therapeutically effective amount of a low combination therapy comprising a botulinum toxin and a TEM generally is in a range of about 0.01 U to about 50 U of botulinum toxin and about 0.1 μg to about 2,000.0 μg of a TEM. In aspects of this embodiment, a therapeutically effective amount of a combined therapy comprising a botulinum toxin and a TEM can be, e.g., about 0.1 U to about 10 U of a botulinum toxin and about 10 μg to about 1,000 μg of a TEM, about 0.1 U to about 10 U of a botulinum toxin and about 10 μg to about 500 μg of a TEM, about 0.1 U to about 10 U of a botulinum toxin and about 10 μg to about 100 μg of a TEM, about 0.5 U to about 10 U of a botulinum toxin and about 10 μg to about 1,000 μg of a TEM, about 0.5 U to about 10 U of a botulinum toxin and about 10 μg to about 500 μg of a TEM, about 0.5 U to about 10 U of a botulinum toxin and about 10 μg to about 100 μg of a TEM, about 1 U to about 10 U of a botulinum toxin and about 100 μg to about 1,000 μg of a TEM, about 1 U to about 10 U of a botulinum toxin and about 100 μg to about 500 μg of a TEM, or about 1 U to about 10 U of a botulinum toxin and about 100 μg to about 100 μg of a TEM.

Dosing can be single dosage or cumulative (serial dosing), and can be readily determined by one skilled in the art. For instance, treatment of a psychological trauma disorder may comprise a one-time administration of an effective dose of a composition disclosed herein. As a non-limiting example, an effective dose of a composition disclosed herein can be administered once to an individual, e.g., as a single injection or deposition at or near the site exhibiting a symptom of a psychological trauma disorder. Alternatively, treatment of a psychological trauma disorder may comprise multiple administrations of an effective dose of a composition disclosed herein carried out over a range of time periods, such as, e.g., daily, once every few days, weekly, monthly or yearly. As a non-limiting example, a composition disclosed herein can be administered once or twice yearly to an individual. The timing of administration can vary from individual to individual, depending upon such factors as the severity of an individual's symptoms. For example, an effective dose of a composition disclosed herein can be administered to an individual once a month for an indefinite period of time, or until the individual no longer requires therapy. A person of ordinary skill in the art will recognize that the condition of the individual can be monitored throughout the course of treatment and that the effective amount of a composition disclosed herein that is administered can be adjusted accordingly.

A composition disclosed herein can be administered to an individual using a variety of routes. Routes of administration suitable for a method of treating a psychological trauma disorder as disclosed herein include both local and systemic administration. Local administration results in significantly more delivery of a composition to a specific location as compared to the entire body of the individual, whereas, systemic administration results in delivery of a composition to essentially the entire body of the individual. Routes of administration suitable for a method of treating a psychological trauma disorder as disclosed herein also include both central and peripheral administration. Central administration results in delivery of a composition to essentially the central nervous system of an individual and includes, e.g., intrathecal administration, epidural administration as well as a cranial injection or implant. Peripheral administration results in delivery of a composition to essentially any area of an individual outside of the central nervous system and encompasses any route of administration other than direct administration to the spine or brain. The actual route of administration of a composition disclosed herein used can be determined by a person of ordinary skill in the art by taking into account factors, including, without limitation, the type of psychological trauma disorder, the location of the psychological trauma disorder, the cause of the psychological trauma disorder, the severity of the psychological trauma disorder, the degree of relief desired, the duration of relief desired, the particular botulinum toxin and/or TEM used, the rate of excretion of the botulinum toxin and/or TEM used, the pharmacodynamics of the botulinum toxin and/or TEM used, the nature of the other compounds to be included in the composition, the particular route of administration, the particular characteristics, history and risk factors of the individual, such as, e.g., age, weight, general health and the like, or any combination thereof.

In an embodiment, a composition disclosed herein is administered systemically to an individual. In another embodiment, a composition disclosed herein is administered locally to an individual. In an aspect of this embodiment, a composition disclosed herein is administered to a nerve of an individual. In another aspect of this embodiment, a composition disclosed herein is administered to the area surrounding a nerve of an individual.

A composition disclosed herein can be administered to an individual using a variety of delivery mechanisms. The actual delivery mechanism used to administer a composition disclosed herein to an individual can be determined by a person of ordinary skill in the art by taking into account factors, including, without limitation, the type of psychological trauma disorder, the location of the psychological trauma disorder, the cause of the psychological trauma disorder, the severity of the psychological trauma disorder, the degree of relief desired, the duration of relief desired, the particular botulinum toxin and/or TEM used, the rate of excretion of the botulinum toxin and/or TEM used, the pharmacodynamics of the botulinum toxin and/or TEM used, the nature of the other compounds to be included in the composition, the particular route of administration, the particular characteristics, history and risk factors of the individual, such as, e.g., age, weight, general health and the like, or any combination thereof.

In an embodiment, a composition disclosed herein is administered by injection. In aspects of this embodiment, administration of a composition disclosed herein is by, e.g., intramuscular injection, intraorgan injection, subdermal injection, dermal injection, intracranial injection, spinal injection, or injection into any other body area for the effective administration of a composition disclosed herein. In aspects of this embodiment, injection of a composition disclosed herein is to a nerve or into the area surrounding a nerve.

In another embodiment, a composition disclosed herein is administered by catheter. In aspects of this embodiment, administration of a composition disclosed herein is by, e.g., a catheter placed in an epidural space.

A composition disclosed herein as disclosed herein can also be administered to an individual in combination with other therapeutic compounds to increase the overall therapeutic effect of the treatment. The use of multiple compounds to treat an indication can increase the beneficial effects while reducing the presence of side effects.

Aspects of the present invention can also be described as follows:

1. A method of treating a psychological trauma disorder in an individual, the method comprising the step of administering to the individual in need thereof a therapeutically effective amount of a composition including a BoNT/A and/or a TEM, wherein administration of the composition reduces a symptom of the psychological trauma disorder, thereby treating the individual.
2. A use of a BoNT/A and/or a TEM in the manufacturing a medicament for treating a psychological trauma disorder in an individual in need thereof.
3. A use of a BoNT/A and/or a TEM in the treatment of a psychological trauma disorder in an individual in need thereof.
4. A method of treating a psychological trauma disorder in an individual, the method comprising the step of administering to the individual in need thereof a therapeutically effective amount of a composition including a botulinum neurotoxin and a TEM, wherein administration of the composition reduces a symptom of the psychological trauma disorder, thereby treating the individual.
5. A use of a botulinum neurotoxin and a TEM in the manufacturing a medicament for treating a psychological trauma disorder in an individual in need thereof.
6. A use of a botulinum neurotoxin and a TEM in the treatment of a psychological trauma disorder in an individual in need thereof.
7. The embodiments of 1 to 6, wherein the TEM comprises a linear amino-to-carboxyl single polypeptide order of 1) a Clostridial toxin enzymatic domain, a Clostridial toxin translocation domain, a targeting domain, 2) a Clostridial toxin enzymatic domain, a targeting domain, a Clostridial toxin translocation domain, 3) a targeting domain, a Clostridial toxin translocation domain, and a Clostridial toxin enzymatic domain, 4) a targeting domain, a Clostridial toxin enzymatic domain, a Clostridial toxin translocation domain, 5) a Clostridial toxin translocation domain, a Clostridial toxin enzymatic domain and a targeting domain, or 6) a Clostridial toxin translocation domain, a targeting domain and a Clostridial toxin enzymatic domain.
8. The embodiments of 1 to 6, wherein the TEM comprises a linear amino-to-carboxyl single polypeptide order of 1) a Clostridial toxin enzymatic domain, an exogenous protease cleavage site, a Clostridial toxin translocation domain, a targeting domain, 2) a Clostridial toxin enzymatic domain, an exogenous protease cleavage site, a targeting domain, a Clostridial toxin translocation domain, 3) a targeting domain, a Clostridial toxin translocation domain, an exogenous protease cleavage site and a Clostridial toxin enzymatic domain, 4) a targeting domain, a Clostridial toxin enzymatic domain, an exogenous protease cleavage site, a Clostridial toxin translocation domain, 5) a Clostridial toxin translocation domain, an exogenous protease cleavage site, a Clostridial toxin enzymatic domain and a targeting domain, or 6) a Clostridial toxin translocation domain, an exogenous protease cleavage site, a targeting domain and a Clostridial toxin enzymatic domain.
9. The embodiments of 1 to 8, wherein the Clostridial toxin translocation domain is a BoNT/A translocation domain, a BoNT/B translocation domain, a BoNT/C1 translocation domain, a BoNT/D translocation domain, a BoNT/E translocation domain, a BoNT/F translocation domain, a BoNT/G translocation domain, a TeNT translocation domain, a BaNT translocation domain, or a BuNT translocation domain.
10. The embodiments of 1 to 9, wherein the Clostridial toxin enzymatic domain is a BoNT/A enzymatic domain, a BoNT/B enzymatic domain, a BoNT/C1 enzymatic domain, a BoNT/D enzymatic domain, a BoNT/E enzymatic domain, a BoNT/F enzymatic domain, a BoNT/G enzymatic domain, a TeNT enzymatic domain, a BaNT enzymatic domain, or a BuNT enzymatic domain.
11. The embodiments of 1 to 10, wherein the targeting domain is a sensory neuron targeting domain, a sympathetic neuron targeting domain, or a parasympathetic neuron targeting domain.
12. The embodiments of 1 to 10, wherein the targeting domain is an opioid peptide targeting domain, a galanin peptide targeting domain, a PAR peptide targeting domain, a somatostatin peptide targeting domain, a neurotensin peptide targeting domain, a SLURP peptide targeting domain, an angiotensin peptide targeting domain, a tachykinin peptide targeting domain, a Neuropeptide Y related peptide targeting domain, a kinin peptide targeting domain, a melanocortin peptide targeting domain, or a granin peptide targeting domain, a glucagon like hormone peptide targeting domain, a secretin peptide targeting domain, a pituitary adenylate cyclase activating peptide (PACAP) peptide targeting domain, a growth hormone-releasing hormone (GHRH) peptide targeting domain, a vasoactive intestinal peptide (VIP) peptide targeting domain, a gastric inhibitory peptide (GIP) peptide targeting domain, a calcitonin peptide targeting domain, a visceral gut peptide targeting domain, a neurotrophin peptide targeting domain, a head activator (HA) peptide, a glial cell line-derived neurotrophic factor (GDNF) family of ligands (GFL) peptide targeting domain, a RF-amide related peptide (RFRP) peptide targeting domain, a neurohormone peptide targeting domain, or a neuroregulatory cytokine peptide targeting domain, an interleukin (IL) targeting domain, vascular endothelial growth factor (VEGF) targeting domain, an insulin-like growth factor (IGF) targeting domain, an epidermal growth factor (EGF) targeting domain, a Transformation Growth Factor-β (TGFβ) targeting domain, a Bone Morphogenetic Protein (BMP) targeting domain, a Growth and Differentiation Factor (GDF) targeting domain, an activin targeting domain, or a Fibroblast Growth Factor (FGF) targeting domain, or a Platelet-Derived Growth Factor (PDGF) targeting domain.

13. The embodiments of 8 to 12, wherein the exogenous protease cleavage site is a plant papain cleavage site, an insect papain cleavage site, a crustacian papain cleavage site, an enterokinase cleavage site, a human rhinovirus 3C protease cleavage site, a human enterovirus 3C protease cleavage site, a tobacco etch virus protease cleavage site, a Tobacco Vein Mottling Virus cleavage site, a subtilisin cleavage site, a hydroxylamine cleavage site, or a Caspase 3 cleavage site.
14. The embodiments of 1 to 13, wherein the Clostridial neurotoxin is a BoNT/A, a BoNT/B, a BoNT/C1, a BoNT/D, a BoNT/E, a BoNT/F, a BoNT/G, a TeNT, a BaNT, a BuNT, or any combination thereof.
15. The embodiments of 1 to 14, wherein the BoNT/A and/or a TEM is administered to an Arnold's nerve or a nerve from the recurrent laryngeal nerve complex.
16. The embodiments of 1 to 14, wherein BoNT/A and/or a TEM is administered using the PREEMPT paradigm.
17. The embodiments of 1 to 14, wherein BoNT/A and/or a TEM is administered to the glabellar complex.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the compounds, compositions, methods or uses of treating a psychological trauma disorder.

Example 1

A patient complains if of being incredibly fearful and nervous when she knows she will be having to deal with a future stressful event. After routine history and physical examination, a physician diagnosis the patient with a post-traumatic stress disorder involving abnormal sympathetic neuron activity that results in abnormal release of epinephrine and noradrenaline, and identifies the nerves and/or muscles involved in the condition. The woman is treated by administration of a composition comprising a BoNT/A as disclosed in the present specification, following the glabellar administration paradigm with 30 U. Alternatively, the woman is treated by administration of a composition comprising a TEM with a therapeutically effective amount. Alternatively, the woman may be treated by administering a composition comprising a TEM and a BoNT/A at 10 U as disclosed in the present specification. The patient's condition is monitored and after about 1 week from treatment, the woman indicates she has decreased fear and nervousness associated with an upcoming stressful event since the treatment. At two and four month check-ups, the woman indicates that she is still experiencing decreased fear and nervousness for upcoming fearful or stressful events. This decrease in fear and nervousness for upcoming fearful or stressful events indicates a successful treatment with the composition comprising a TEM and a BoNT/A as disclosed in the present specification.

A similar therapeutic effect can be achieved with a sub-optimal amount of any of the Clostridial toxins disclosed herein.

Example 2

A patient complains having a difficult time falling and staying asleep, being more irritable and having outbursts of anger, having difficulty concentrating, feeling constantly "on guard" like danger is lurking around every corner, being "jumpy," having a difficult time concentrating, having "flashbacks" to combat, and feeling as log his life will be cut short.

The man is thoroughly examined by a doctor and diagnosed with post traumatic stress disorder. The doctor concludes that botulinum toxin therapy is appropriate. A total of 100 Units of Botox® is administered to the sphenopalatine ganglion nerves, with an additional 100 Units administered to the face, head and neck. Alternatively, the man is treated by administration of a therapeutically effective amount of a composition comprising a TEM. Alternatively, the man may be treated by administering a composition comprising a TEM and a decreased amount of BoNT/A relative to BoNT/A alone. Within days, the patient reports a decrease in his symptoms. The patient is evaluated at three months to determine whether another round of administrations is necessary.

Example 3

A former soldier complains having a difficult time falling and staying asleep, being more irritable and having outbursts of anger, having difficulty concentrating, feeling constantly "on guard" like danger is lurking around every corner, being "jumpy," having a difficult time concentrating, having "flashbacks" to combat, and feeling as log his life will be cut short.

The man is thoroughly examined by a doctor and diagnosed with post traumatic stress disorder. The doctor concludes that a combination of botulinum toxin therapy and TEM therapy is appropriate. A total of 100 Units of Botox® is administered to the sphenopalatine ganglion nerves, with an additional 100 Units administered to the face, head and neck. Within days, the patient reports a decrease in his symptoms. The patient is evaluated at three months to determine whether another round of administrations is necessary.

Example 4

A student is a assaulted while walking back to her dorm room from the campus library. The woman complains of a markedly diminished interest in significant activities; a feeling detachment and estrangement from others in her life; she has a sense of a foreshortened future; avoidance of the library; fear of walking alone even during the day; difficulty concentrating; trouble sleeping and nightmares.

The woman is thoroughly interviewed and examined by a doctor and is diagnosed with traumatic stress disorder. The doctor concludes that botulinum toxin therapy is appropriate. Botox® is administered to 31 sites in the head, neck and shoulders. Specifically, 155 units of Botox® is administered to: the frontalis at about twenty units divided among four sites of administration; to the corrugator at about ten units divided among two sites of administration; to the procerus at about five units to one site of administration; to the occipitalis at about thirty units divided among six sites of administration to about forty units divided among eight sites of administration; to the temporalis at about forty units divided among eight sites of administration up to fifty units divided among ten sites of administration; to the trapezius at about thirty units divided among six sites of administration up to about fifty units divided among ten sites of administration and to the cervical paraspinal muscles at about twenty units divided among four sites of administration. Within days, the patient reports a decrease in her symptoms. The patient is evaluated at three months to determine whether another round of administrations is necessary.

Example 5

A student is a assaulted while walking back to her dorm room from the campus library. The woman complains of a markedly diminished interest in significant activities; a feeling detachment and estrangement from others in her life; she has a sense of a foreshortened future; avoidance of the library; fear of walking alone even during the day; difficulty concentrating; trouble sleeping and nightmares.

The woman is thoroughly interviewed and examined by a doctor and is diagnosed with traumatic stress disorder. The doctor concludes that a combination botulinum toxin therapy with TEM therapy is appropriate. Botox® and a TEM are co-administered to 31 sites in the head, neck and shoulders. Specifically, 50 units of Botox® and a 30-fold molar ratio of a TEM are administered to: the frontalis at divided among four sites of administration; to the corrugator divided among two sites of administration; to the procerus at one site of administration; to the occipitalis at six sites to eight sites of administration; to the temporalis at eight sites to ten sites of administration; to the trapezius at six sites to ten sites of administration and to the cervical paraspinal muscles at four sites of administration. Within days, the patient reports a decrease in her symptoms. The patient is evaluated at three months to determine whether another round of administrations is necessary.

Example 6

A woman is caught in a severe storm while visiting relatives in Georgia. She survives a tornado by hiding in a closet on the ground floor, but most of the house is destroyed and the next morning she learns that many neighbors were killed. Two months after returning home, the woman complains of a feeling detachment and estrangement from others in her life; a sense of a foreshortened future; difficulty concentrating; trouble sleeping and nightmares. She also develops a strong fear of rain, thunder, and loud winds.

The woman is thoroughly interviewed and examined by a doctor and is diagnosed with traumatic stress disorder. The doctor concludes that botulinum toxin therapy is appropriate. A therapeutically effective amount of botulinum toxin is administered to the sphenopalantine ganglion nerves, with an additional amount administered to the face, head and neck. Within days, the patient reports a decrease in her symptoms. The patient is evaluated at three months to determine whether another round of administrations is necessary.

Example 7

A dog is caught in a severe storm and survives a tornado by hiding in a closet with his owner. Two month later, the dog is constantly agitated, vomits regularly, and curls up and whimpers at even moderate sounds. The dog is examined by a veterinarian who determines the dog is suffering from PTSD. The veterinarian administers a therapeutically effective amount of BoNT/A to the glabellar complex. Alternatively, the veterinarian could administer a TEM or a combination of BoNT/A and TEM. One week later, the PTSD symptoms are decreased. The dog is evaluated three months later to determine if more treatment is necessary. Alternatively, the veterinarian could administer according to a PREEMPT paradigm.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A method of treating at least one symptom of post-traumatic stress disorder in a patient in need thereof, the method comprising the step of administering to the patient a therapeutically effective amount of a composition including a botulinum neurotoxin serotype A (BoNT/A), wherein administration is to the glabellar complex; wherein administration of the composition decreases the at least one symptom of the post-traumatic stress disorder; and wherein the at least one symptom of post-traumatic stress disorder comprises total or partial amnesia of a traumatic event, flashbacks or nightmares wherein the patient re-experiences the traumatic event, avoidance of stimuli associated with the traumatic event, increased arousal including difficulty falling or staying asleep, anger, hyper-vigilance, or combinations thereof.

2. The method of claim 1, wherein the composition is additionally administered to: the frontalis at divided among four sites of administration; to the occipitalis at six sites to eight sites of administration; to the temporalis at eight sites to ten sites of administration; to the trapezius at six sites to ten sites of administration and to the cervical paraspinal muscles at four sites of administration.

* * * * *

UNITED STATES PATENT AND TRADEMARK OFFICE

CERTIFICATE OF CORRECTION

PATENT NO. : 9,764,009 B2
APPLICATION NO. : 13/495605
DATED : September 19, 2017
INVENTOR(S) : Kenton B. Abel et al.

It is certified that error appears in the above-identified patent and that said Letters Patent is hereby corrected as shown below:

On the Title Page

Item (56), in Column 2, under “Other Publications”, Line 15, delete “Pharmceutical” and insert -- Pharmaceutical --, therefor.

Item (56), in Column 2, under “Other Publications”, Line 17, delete “Nerotoxins” and insert -- Neurotoxins --, therefor.

In the Specification

In Column 13, Line 23, delete “$6.0\times10^{-1}$” and insert -- $6.0\times10^{-4}$ --, therefor.

In Column 26, Line 38, delete “less that” and insert -- less than --, therefor.

In Column 35, Line 3, delete “crustacian” and insert -- crustacean --, therefor.

In Column 35, Line 34, delete “if of” and insert -- of --, therefor.

In Column 37, Line 49, delete “sphenopalantine” and insert -- sphenopalatine --, therefor.

Signed and Sealed this
Twenty-first Day of November, 2017

Joseph Matal
*Performing the Functions and Duties of the*
*Under Secretary of Commerce for Intellectual Property and*
*Director of the United States Patent and Trademark Office*